US005399701A

United States Patent [19]
Janulis

[11] Patent Number: 5,399,701
[45] Date of Patent: Mar. 21, 1995

[54] FLUORINE-CONTAINING CHIRAL SMECTIC LIQUID CRYSTALS

[75] Inventor: Eugene P. Janulis, Mahtomedi

[73] Assignee: Minnesota Mining and Manufacturing Company, St. Paul, Minn.

[21] Appl. No.: 92,019

[22] Filed: Jul. 15, 1993

Related U.S. Application Data

[60] Division of Ser. No. 703,393, May 21, 1991, Pat. No. 5,254,747, which is a division of Ser. No. 373,898, Jun. 29, 1989, abandoned, which is a division of Ser. No. 53,551, May 29, 1987, Pat. No. 4,886,619, which is a continuation-in-part of Ser. No. 879,988, Jun. 30, 1986, abandoned.

[51] Int. Cl.$^6$ .......................................... C07D 239/02
[52] U.S. Cl. .................................................. 546/298
[58] Field of Search ........................................ 546/298

[56] References Cited

U.S. PATENT DOCUMENTS

| | | | |
|---|---|---|---|
| 4,001,137 | 1/1977 | Steinstrasser et al. | 252/299 |
| 4,011,173 | 3/1977 | Steistraser | 252/299 |
| 4,113,647 | 9/1978 | Coates et al. | 252/299 |
| 4,202,791 | 5/1980 | Sato et al. | 252/299 |
| 4,256,656 | 3/1981 | Beguin et al. | 260/465 |
| 4,330,426 | 5/1982 | Eidenschink et al. | 252/299 |
| 4,367,924 | 1/1983 | Clark et al. | 350/334 |
| 4,393,231 | 7/1983 | Misaki et al. | 560/73 |
| 4,400,293 | 8/1983 | Romer et al. | 252/299 |
| 4,439,015 | 3/1984 | Rich et al. | 252/299 |
| 4,481,149 | 11/1984 | Misaki et al. | 260/465 |
| 4,564,694 | 1/1986 | Hirai et al. | 560/1 |
| 4,572,794 | 2/1986 | Eidenschink et al. | 252/299 |
| 4,576,732 | 3/1986 | Isogai et al. | 252/299 |
| 4,592,858 | 6/1986 | Higuchi et al. | 252/299 |

(List continued on next page.)

FOREIGN PATENT DOCUMENTS

| | | |
|---|---|---|
| 0047877 | 8/1981 | European Pat. Off. . |
| 0163229 | 12/1985 | European Pat. Off. . |
| 0181601 | 5/1986 | European Pat. Off. . |

(List continued on next page.)

OTHER PUBLICATIONS

CA 110: 105603 1988 (Abstract of Barbera, Ferroelectrics, vol.-date 1987, 85, 405-13.)
CA 109: 160774 1988 (Abstract of Sakurai, JP 63045258).
CA 109: 83683 1988 (Abstract of Sakurai, JP63017848).
CA 103: 62974 1985 (Abstract of Barbera, Mol. Cryst. Liq. Cryst 126 (2-4) 259-68).
CA 87: 4816 1976 (Abstract of Parlyuchenko, Mol. Cryst Liq Cryst 37 (1-4) 35-46).
CA 81: 55350 1974 (Abstract of Nash, Mol. Cryst Liq Cryst 25(3/4) 299-321).
*Jap. Jornal of Applied Physics*, vol. 22, No. 10, Oct. 1983, pp. 1661-1663.
*Ferroelectrics*, vol. 58, pp. 3-7, 1984.
*Molecular Crystals Liquid Crystals*, vol. 47, 1978, pp. 1-5.
*Molecular Crystals Liquid Crystals*, vol. 67, 1981, pp. 235-240.
"The Silicon Liquid-Crystal Light Value", *J. Appl. Phys.*, 57(4), 1985, pp. 1356-1368.
"Smectic Liquid Crystal from (Perfluorodecyl)decane", *Molecular Crystals Liquid Crystals*, vol. 2 (3-4) 1985, pp. 111-119.
*Molecular Crystals Liquid Crystals*, 1984, pp. 114, 237-247.

(List continued on next page.)

*Primary Examiner*—Johann Richter
*Assistant Examiner*—Catherin S. Kilby Scalzo
*Attorney, Agent, or Firm*—Gary Griswold; Walter N. Kirn; Carole Truesdale

[57] ABSTRACT

Compounds are provided which comprise a fluorocarbon terminal portion and a chiral hydrocarbon terminal portion, said terminal portions being connected by a central core, said compounds having tilted smectic mesophases or having latent tilted smectic mesophases which develop when said compounds having said latent mesophases are in admixture with said compounds having tilted smectic mesophases or said compounds having latent tilted smectic mesophases.

2 Claims, No Drawings

U.S. PATENT DOCUMENTS

| | | | |
|---|---|---|---|
| 4,613,209 | 9/1986 | Goodby et al. | 350/350 |
| 4,614,608 | 9/1986 | Le Barny et al. | 252/299 |
| 4,617,140 | 10/1986 | Eidenschink et al. | 252/299 |
| 4,668,427 | 3/1987 | Saito et al. | 252/299 |
| 4,780,242 | 10/1988 | Miyazawa et al. | 252/299 |
| 4,816,178 | 3/1989 | Katagiri et al. | 252/299 |
| 4,816,596 | 3/1989 | Langlois | 558/423 |
| 4,837,364 | 6/1989 | Desbois et al. | 568/43 |
| 4,876,027 | 11/1989 | Yoshinaga et al. | 252/299 |
| 4,879,060 | 11/1989 | Shionozaki et al. | 252/299 |
| 4,914,224 | 4/1990 | Shoji et al. | 560/65 |

FOREIGN PATENT DOCUMENTS

| | | |
|---|---|---|
| 3332692 | 9/1983 | Germany . |
| 57-165334 | 10/1982 | Japan . |
| 2162515 | 6/1985 | United Kingdom . |

OTHER PUBLICATIONS

*J. Am. Chem. Soc.*, vol. 86, 1964, pp. 964–965.

*Jap. Jornal of Applied Physics*, vol. 24, No. 11, Nov. 1985, pp. 1389–1393.

J. W. Goodby and T. M. Leslie, "Some Novel Ferroelectric Smectic Liquid Crystals", *Liquid Crystals & Ordered Fluids*, vol. 4, pp. 1–42, 1977.

Gray, G. W., *Liquid Crystals & Plastic Crystals*, vol. 1, 1974, pp. 142–143.

Zverkova, T. I. et al., *Advances in Liquid Crystal Research & Applications*, Pergamon Press, Oxford (1980) pp. 991–995.

LeBarny, P. et al., *Molecular Crystals and Liquid Crystals*, vol. 127, 1985, pp. 413–429.

Streitweiser, A. et al.; *Introduction to Organic Chemistry*, 1976, pp. 378–380, 480, 837.

Sirutkaitis, P. et al., *Advances in Liquid Crystal Research and Applications*, Bata, L. Pargamon Press, Oxford, 1980, pp. 1023–1028.

FLUORINE-CONTAINING CHIRAL SMECTIC LIQUID CRYSTALS

This is a division of U.S. patent application Ser. No. 07/703,393, filed May 21, 1991, now U.S. Pat. No. 5,254,747, which is a division of U.S. patent application Ser. No. 07/373,898, filed Jun. 29, 1989, abandoned, which is a division of U.S. patent application Ser. No. 07/053,551, filed May 29, 1987, now U.S. Pat. No. 4,886,619, which is a continuation-in-part of application Serial No. 6/879,988, filed Jun. 30, 1986, now abandoned.

FIELD OF THE INVENTION

This invention relates to chiral smectic liquid crystal compounds which are optically active and exhibit ferroelectric behavior. Such compounds are particularly useful in surface-stabilized ferroelectric liquid crystal display devices.

BACKGROUND OF THE INVENTION

A recent advance in the liquid crystal art has been the utilization of tilted chiral smectic materials in a surface-stabilized device geometry to give very high speed bistable switching not found in devices using nematic liquid crystals. U.S. Pat. No. 4,367,924 (Clark et al.) discloses the use of chiral smectic C or chiral smectic H liquid crystal materials in a device with response times of 1000 to 10,000 times faster than previously attained with other liquid crystalline compounds. Clark et al. describe the use of two ferroelectric, i.e., tilted, chiral smectic, liquid crystal compounds: (+)-p-[n-decyloxybenzylidene]-p'-amino-(2-methylbutyl)cinnamate (DOBAMBC) and (+)-p-[n-hexyloxy-benzylidene]-p'-amino-(2-chloropropyl)cinnamate (HHOBACPC). These compounds have a number of shortcomings including chemical instability and UV sensitivity. Their inherent short pitch length and high birefringence severely restrict the design parameters of the display devices and their high transition temperatures require the use of thermal management techniques.

In Ferroelectrics, Vol. 58, p. 3-7, 1984, Keller describes phenyl benzoate ester liquid crystal materials, where one of the alkyl groups attached to a phenyl ring is optically active, i.e., chiral. Some of these materials possess a chiral smectic C mesophase and show ferroelectric behavior. Of the compounds that are ferroelectric liquid crystals, however, most also show an undesired cholesteric mesophase and those that do not show the cholesteric mesophase have very narrow ferroelectric temperature ranges.

U.S. Pat. Nos. 4,393,231 and 4,481,149 (Misaki et al.) describe achiral perfluoroalkyl substituted phenyl benzoate ester liquid crystal compounds. Such achiral compounds cannot exhibit chiral smectic mesophases and cannot be used as ferroelectric liquid crystal materials.

V. V. Titov and co-workers have published a number of papers describing fluorinated liquid crystal materials. Titov et al. postulated that replacement of hydrogen atoms with fluorine atoms might cause a change of intermolecular interaction and consequently mesomorphic properties owing to geometric and electronic factors. Two representative papers, (*Molecular crystals Liquid Crystals*, Vol. 67, pp 235-240 (1981) and Vol. 47, pp 1-5 (1978)), describe four partially fluorinated alkoxy and several perfluorinated alkyl and alkoxy substituted liquid=crystal materials. None of these compounds are optically active and, thus, cannot possess ferroelectric properties.

U.S. Pat. No. 4,256,656 (Beguin et al.) discloses substituted phenyl benzoate esters where one of the phenyl rings is fluorinated. These compounds are not chiral and therefore cannot exhibit ferroelectric behavior. Also, ring fluorination enhances the formation of the undesired nematic mesophase.

Mahler, Walter, et al., in "Smectic Liquid Crystal from (Perfluorodecyl)decane," *Mol. Cryst. Liq. Cryst. Letters*, Vol. 2(3-4), 1985, pp 111-119, disclose the smectogenic ability of (perfluorodecyl)decane, $F(CF_2)_{10}(CH_2)_{10}H$. This compound exhibits a smectic B liquid crystal phase, but is not chiral and therefore cannot exhibit ferroelectric behavior.

SUMMARY OF THE INVENTION

The present invention provides compounds comprising a fluorocarbon terminal portion and a chiral hydrocarbon terminal portion, the terminal portions being connected by a central core, the compounds having tilted smectic mesophases or having latent tilted smectic mesophases which develop when said compounds having said latent mesophases are in admixture with said compounds having tilted smectic mesophases or other said compounds having latent tilted smectic mesophases. These compounds have suppressed cholesteric, i.e., chiral nematic, mesophases. The fluorocarbon terminal portion can be represented by the formula $-DC_qF_{2q}X$ where X is hydrogen or fluorine, q is 1 to 20, and D is

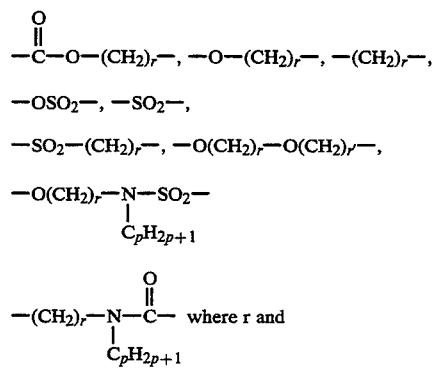

where r and r' are independently 1 to 20 and p is 0 to 4. These compounds have greatly enhanced smectogenic properties, lower birefringences, and longer pitch length than their non-fluorine-containing analogues, as well as, fast switching times. These properties make these materials useful in a broader range of devices having less restrictive design parameters than with previously known ferroelectric liquid crystal compounds. Further, mixtures of the compounds of the invention can be formulated to provide desired transition temperatures and broad mesophase temperature ranges. The present invention further provides precursor compounds useful in the preparation of the ferroelectric liquid crystals.

The present invention still further provides a process for preparing the ferroelectric liquid crystals of the invention. The present invention also relates to ferroelectric liquid crystal devices containing the chiral smectic fluorinated compounds.

DETAILED DESCRIPTION OF THE INVENTION

The present invention relates to chiral compounds having fluorine-containing terminal groups and compounds related thereto for use as liquid crystal materials. Compounds of this invention are tilted chiral smectic, i.e., ferroelectric, liquid crystals, liquid crystal enhancers, or liquid crystal modifiers. Tilted chiral smectic liquid crystal molecules, such as chiral smectic C or H, are known to be ferroelectric, i.e., possessing a permanent polarization perpendicular to the director or long axis of the molecule. Because these chiral smectic materials exhibit a non-zero net polarization in the bulk, there is a stronger coupling of this polarization with an applied electric field than when there is only dielectric anisotropic coupling. It is this stronger coupling in an applied electric field that provides the molecules with an ability to orient readily with greatly reduced switching time.

Ferroelectric or tilted chiral smectic molecules orient themselves in layers. Because of the chirality of ferroelectric materials, the directors spiral about an axis normal to the layers. The distance required for a complete $2\pi$ rotation of the director is called the pitch length. To produce a surface-stabilized ferroelectric liquid crystal device as in U.S. Pat. No. 4,367,924 (Clark et al.), it is necessary to suppress the formation of this $2\pi$ rotation, i.e., helix. This is accomplished by using the appropriate boundary conditions and geometry as are well-known in the art.

In fabricating such a surface-stabilized ferroelectric liquid crystal device, the ferroelectric liquid crystal materials or mixtures thereof are placed between two bounding plates, usually glass, the inside surfaces of which have electrodes applied and at least one of which is transparent. The electrode configuration can be a single electrode, a patterned electrode, x-y electrodes forming addressable pixels or the like. The boundary conditions on the inside surfaces of the plates, next to the ferroelectric liquid crystal material(s) must be prepared by shearing or rubbing an applied polymer alignment layer, or the like, as is well-known in the art, so as to orient the director of the ferroelectric liquid crystal molecules parallel to the glass plates, and to orient the layers of the bulk ferroelectric liquid crystal perpendicular to the glass plates. The spacing between the plates is such that the plates are separated by a distance of less than the pitch of the helix, resulting in suppression of helix formation. The plates are sealed around the edges and a driving electrical circuit is connected to the plate electrodes. Two stable states of director orientation exist, each state dependent upon the direction of the applied electric field across the conductive electrodes. In the first stable state, the polarization is aligned in one direction, while in the other stable state the director has been rotated through twice the material tilt angle and the polarization is in the direction opposite to that in the first stable state. The "material tilt angle" is that angle between the director and the layer normal. The device is placed between crossed polarizers and oriented with one of the polarizers aligned with one of the stable states. Application of an electric field changes the transmission of the device from, for example, a minimally transmitting state to a highly transmitting state and reversal of the field will return the device to the minimally transmitting state. The result is a fast switching ferroelectric liquid crystal device wherein the helix is unwound even in the absence of an electric field and which device can be bistable.

The compounds of this invention are also useful in non-surface stabilized ferroelectric liquid crystal display devices. Such non-surface-stabilized devices are fabricated in the same manner as the surface-stabilized devices except that the distance between the plates is greater than the helix pitch length. These non-surface stabilized devices can never be bistable because the material returns to a helical structure in the absence of an applied electrical field.

The compounds of this invention are also useful in optically addressed liquid crystal display devices. In such devices, one of the plates is replaced with a structure containing a photoconductive material such as cadmium sulfide and the device is optically addressed, i.e., activated by light. Such a device, described for use with nematic liquid crystal material is disclosed by Effort, U., et al., in "The Silicon Liquid Crystal Light Valve, *J. Appl. Phys.* 57(4), 1985, pp 1356–1368, which is incorporated herein by reference. This device is equally suitable for use with the chiral smectic liquid crystal materials of the present invention.

Light transmission through a surface-stabilized device with two polarizers is represented by the following equation:

$$I = I_0[\sin^2(4\Theta)][\sin^2(\pi \Delta nd/\lambda)]$$

where
Io = transmission through parallel polarizers
$\Theta$ = material tilt angle
$\Delta n$ = liquid crystal birefringence
d = device spacing
$\lambda$ = wavelength of light To maximize the transmission, both $\sin^2(4\Theta)$ and $\sin^2(\pi \Delta and/\lambda)$ must be at maximum. This occurs when each $\sin^2$ term equals one. The first term will be a maximum when $4\Theta = \pi/2$ or when $\Theta = 22.5°$. This is a function of the liquid crystal and is constant for a given material at a given temperature. The compounds of this invention have typical $\Theta$ values from 17° to 40°. The second term is maximum when $\pi \Delta and/\lambda = \pi/2$ or $\Delta nd = \lambda/2$.

This demonstrates the criticality of the low birefringence of the materials of this invention, which low birefringence allows a larger device thickness, d, for a given wavelength of light. The long pitch length of the materials of this invention make it possible to take advantage of the above relationship. Thus, because of the longer pitch length and lower birefringence of these materials, compared to presently available materials, a larger plate spacing is possible while still maximizing transmission, allowing easier device construction.

The fluorine-containing chiral compounds of the present invention can be represented by the general formula:

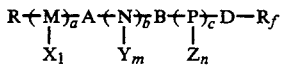

where M, N, and P are each independently

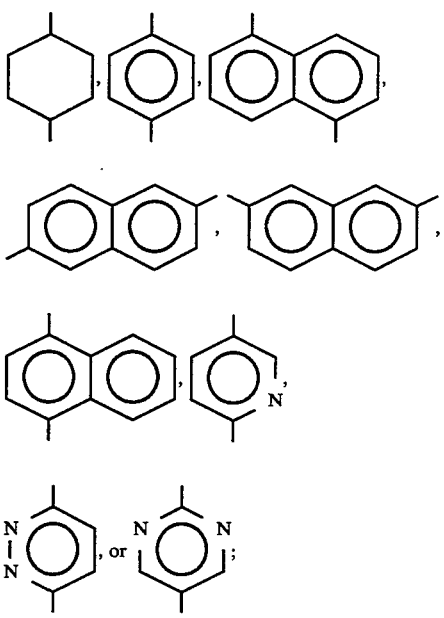

a, b, and c are each independently zero or an integer of from 1 to 3 with the proviso that the sum of a+b+c be at least 2;

each A and B are independently nil,

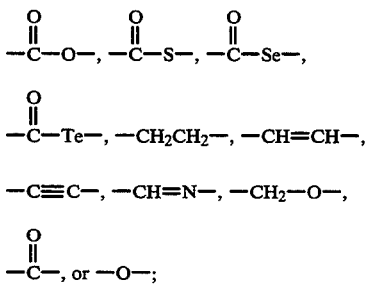

each X, Y and Z are independently —H, —Cl, —F, —OCH$_3$, —CH$_3$, —OH, —Br, —I, —NO$_2$, or —CN; each l, m, and n are independently zero or an integer of 1 to 4;

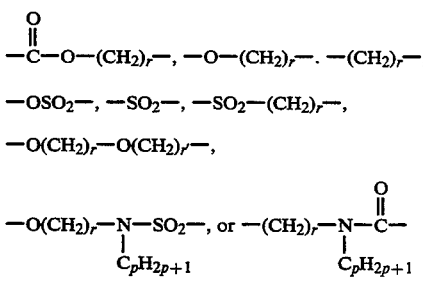

where r and r' are independently l to 20, and p is 0 to 4; R is —OC$_q$H$_{2q}$—OC$_q$, H$_{2q'+1'}$ —C$_q$H$_{2q}$—O—C$_q$, H$_{2'+1'}$—C$_q$H$_{2q}$—R', —O—C$_q$H$_{2-q}$—R',

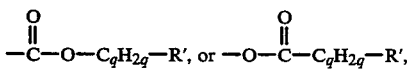

where R' is —Cl, —F, —CF$_3$, —NO$_2$, —CN, —H,

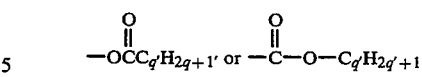

and q and q' are independently 1 to 20 with the proviso that R is chiral; and

R$_f$ is —C$_q$F$_{2q}$—X or —C$_q$F$_{2q}$—O—C$_q$, F$_{2q}$, —X, where X is H or F, and q and q' are independently 1 to 20.

Several of the compounds of the above formula were observed to not have smectic phases as single components upon cooling from the isotropic phase. Upon further investigation it was found that these compounds, when mixed with other liquid crystals or other compounds of the above formula, did show a desired tilted smectic phase and, thus, exhibit a phenomenon termed herein "latent tilted smectic mesophases". It is suspected that these compounds may have monotropic smectic phases at temperatures below their crystallization points. By the Phase Rule for mixtures, these smectic phases will appear at different mixture ratios, which ratios can be readily determined by those skilled in the art.

Chiral smectic liquid crystal compounds of this invention have a number of desirable properties. Chain fluorination induces a higher order in the molecule than the non-fluorine containing analogs and thus cholesteric mesophases are lost and smectic mesophases are introduced or enhanced. It is believed that the incompatibility of the fluorophilic portions, i.e., the fluorine-containing terminal portions, and the fluorophobic portions, i.e., the hydrocarbon core and terminal portions, of the materials lead to the higher ordering. This belief is buttressed by the fact that introduction of a hydrogen atom on the terminal carbon atom of a perfluorinated chain generally results in a narrower smectic phase range and a lowering of the clearing point due to unfavorable dipole-dipole interactions at the smectic layer interface.

The compounds of this invention have longer pitch lengths and lower birefringences than the non-fluorinated analogs and, thus, are very useful in the fabrication of ferroelectric liquid crystal devices. In such devices, at thicknesses less than about 50 microns, unusual chiral smectic textures are observed by optical microscopy, the textures generally being devoid of pitch lines.

It is suspected that the packing of the liquid crystal materials of the invention is in an interdigitated structure. Cross-sectional molecular areas of fluorocarbon chains are about 1½ to 2 times those of hydrocarbon chains. Thus, the structure of each layer can have close packing with interdigitation of the hydrocarbon core and terminal chains and the outer portion of each layer formed by the fluorocarbon chains. This hypothesis is further suggested by small angle X-ray scattering measurements which indicate that layer spacing is only somewhat greater, i.e., about 20 to 60 percent greater than the extended length of the molecule for a given material at a given temperature.

The materials of this invention have good chemical stability towards water, weak acids and weak bases. They do not undergo degradation during normal use in a device. They are photo-chemically stable in that they do not easily undergo photochemical reactions. They are generally colorless compounds with no absorption in the visible spectrum.

When these compounds are used in mixtures, a lowering of transition temperatures is observed accompanied by an insignificant clearing point temperature change which leads to a broader temperature range for the mesophases observed.

For the phenyl benzoate ester series of compounds, the smectic-mesophases are observed for shorter alkyl and alkoxy terminal chain lengths than for the non-fluorinated analogs.

The novel precursor compounds, useful in the preparation of the ferroelectric liquid crystals of the invention, are those which can Be represented by the formula:

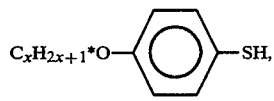

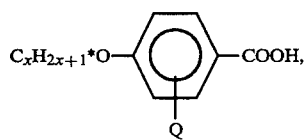

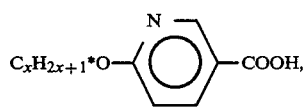

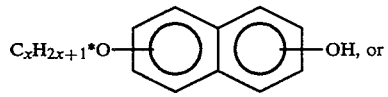

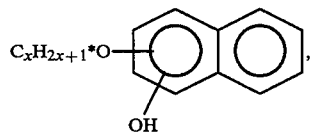

where Q is —Cl or —OCH$_3$, x is 4 to 20 and the compounds are chiral, and compounds represented by the formula

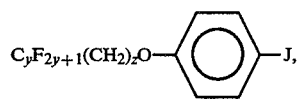

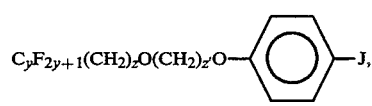

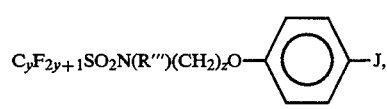

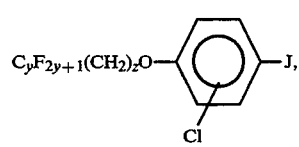

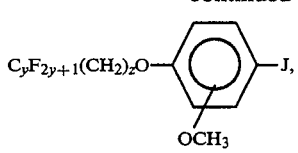

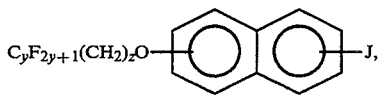

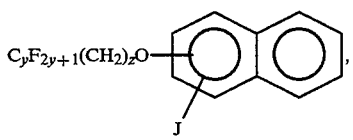

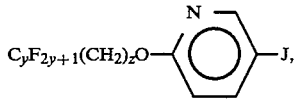

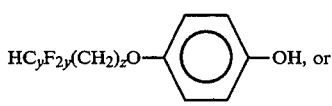

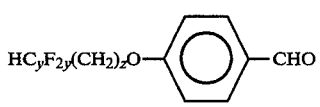

where J is —OH, —COOH, or —CHO, y is 1 to 20, z and z' are independently 1 to 20, and R''' is an alkyl group having 1 to 4 carbon atoms.

The compounds of the invention can be readily prepared by (1) mixing at least one compound represented by the formula

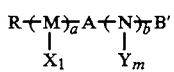

with at least one compound represented by the formula

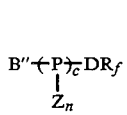

or (2) mixing at least one compound represented by the formula

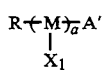

with at least one compound represented by the formula

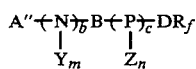

where M, N, and P are each independently

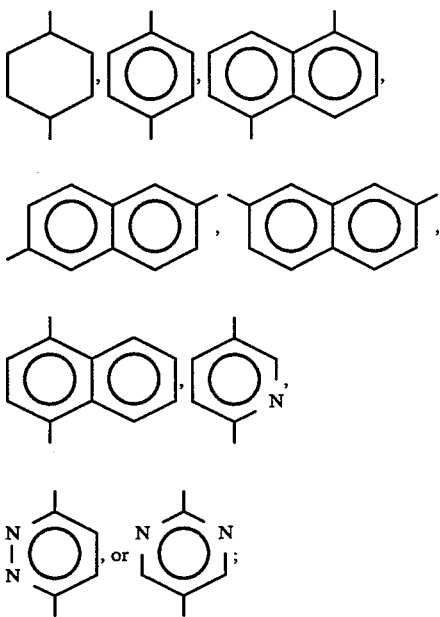

a, b, and c are each independently zero or an integer of from 1 to 3 with the proviso that the sum of a+b+c be at least 2;

each A and B are independently nil,

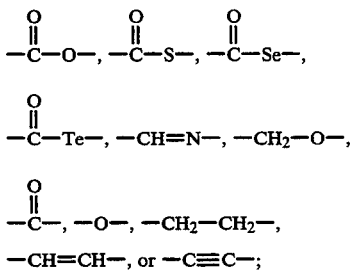

—CH=CH—, or —C≡C—;

each A,' A", B' and B" are independently —OH, —COOH, —SH, —SeH, —TeH, —NH₂, —COCl, —CHO, or —CH₂COOH, with the proviso that A' can enter into an addition or condensation reaction with A" and B' can enter into an addition or condensation reaction with B";

each X, Y and Z are independently —HH, —Cl, —F, —OCH₃, —OH, —Br, —I, —CHH₃, —NO₂ or —CN;

each l, m and n are independently zero or an integer of 1 to 4;

R is —OC$_q$H$_{2q}$ —OC$_q$, H$_{2q'+1}$,
—C$_q$H$_{2q}$—O—$_q$, H$_{2q'+1}$, —C$_q$H$_{2q}$—R', —O—C$_q$H$_{2q'}$—R',

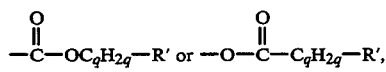

where R' is —H, —Cl, —F, —CF₃, —NO₂, —CN,

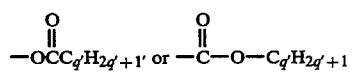

and q and q' are independently 1 to 20, with the proviso that R is chiral;

D is

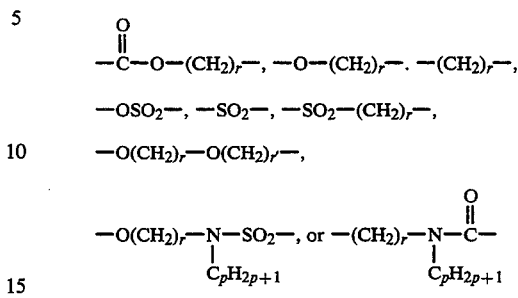

—O(CH₂)$_r$—O(CH₂)$_{r'}$—, $$-O(CH_2)_r-N-SO_2-, \text{ or } -(CH_2)_r-N-C- \\ \phantom{-O(CH_2)_r-N-SO_2-, \text{ or }}| \phantom{-(CH_2)_r-N-}| \\ \phantom{-O(CH_2)_r-N-SO_2-, \text{ or }}C_pH_{2p+1} \phantom{-(CH_2)}C_pH_{2p+1}$$

where r and r' are independently 1 to 20, and p is 0 to 4; R$_f$ is —C$_q$F$_{2q}$—X or —C$_q$F$_{2q}$—O—C$_q$, F$_{2q}$, —X, where X is H or F, and q and q' are independently 1 to 20; and allowing said A' and A" or B' or B" to react in the presence of suitable coupling agents as is well-known to those skilled in the art For example, if A', or B', is —COOH and A", or B", is —OH the compounds are coupled in a suitable solvent system using N,N'-dicyclohexylcarbodiimide and 4-(N,N-dimethylamino)pyridine catalyst; if A', or B', is —COCl and A", or B", is —OH, —SH, —SeH, or —TeH, the compounds are coupled in a suitable solvent using triethylamine base; if A', or B', is —CHO and A", or B" is —NH₂, the compounds are coupled in anhydrous solvent using an acid catalyst under reflux.

The compounds of this invention are either liquid crystals themselves and can be used as such or in mixtures with other liquid crystals; or if not liquid crystalline above their crystallization temperatures, are useful in admixture with other liquid crystals to modify or enhance their properties. The compounds of the invention are also useful when in admixture with pleochroic dyes in a guest-host mixture. These mixtures provide color to the liquid crystal devices, enhance the contrast and brightness, and eliminate the need for one device polarizer as is well known in the art.

EXAMPLES

In the following examples, the trifluoromethylsulfonate esters were prepared using the method of U.S. Pat. No. 3,419,595 except that trifluoromethanesulfonic anhydride was used in place of trifluoromethanesulfonyl fluoride; the S-2-methylbutyl, S-4-methylhexyl, and R-1-methylheptyl tosylates were prepared following the reaction scheme in *Mol. Cryst. Liq. Cryst.*, 1984, 114, 237–247; the 4-benzyloxy-4'-hydroxybiphenyl was prepared as described in U.S. Pat. No. 4,614,609, Example 25(i) except that benzyl chloride was substituted for the (+)-2-methylbutyl bromide; the 2-chloro-4-methylpentanoic acid was prepared as described in *J. Org. Chem.*, 51, 1986, 242–245; the S-2-methylbutyl-4-hydroxybenzoate was prepare as described in *Liquid Crystals and Ordered Fluids*, ed. Griffin, A. C. et al., 4, 1984, p. 1–42; the S-4-(2-methylbutyl)phenol was prepared as described in U.S. Pat. No. 4,195,916; all acid chlorides were prepared by reacting the appropriate carboxylic acid with an excess of thionyl chloride under reflux, followed by removal of the excess thionyl chloride and distillation or recrystallization of the acid chloride; and all alkyl bromides were prepared by treating the corresponding alcohol with bromine in the presence of triphenylphosphine, as disclosed in *J. Am. Chem. Soc.*, 86, 1964, p. 964–965.

Examples 1–68 describe procedures for preparing intermediate compounds useful in preparing the liquid crystal compounds of this invention. Examples 69–139 describe preparation of the liquid crystal compounds of this invention. Examples 140–169 describe mixture formulations with materials possessing a latent chiral smectic mesophase. Examples 170–175 describe multicomponent mixture formulations utilizing liquid crystal compounds of this invention in liquid crystal devices.

EXAMPLE 1

Sodium methylate was prepared by reacting sodium (2.3 g, 0.1 mol) with 100 ml anhydrous methanol. To the sodium methylate was added methyl 4-hydroxybenzoate (15.2 g, 0.1 mol). Excess methanol was removed under reduced pressure and toluene was added and removed under reduced pressure to remove any residual methanol. The solid residue was dissolved in 2:1 toluene-dimethylformamide and S-4-methylhexyl bromide (17.9 g, 0.1 mol) was added as a single portion and the mixture was refluxed for 1 day. The reaction product was cooled and washed 3 times with 100 ml water. The organic layer was dried over anhydrous $MgSO_4$, filtered, and concentrated. This crude methyl S-4-(4-methylhexyloxy)benzoate was refluxed in 100 ml of 10% aqueous sodium hydroxide for 1 day. The reaction product was cooled to room temperature (25° C.) and acidified with concentrated aqueous HCl. The precipated solid was collected by filtration and washed several times with cool water. This material was purified by recrystallization from ethanol-water. S-4-(4-Methylhexyloxy)benzoic acid (20 g, 85% yield) was obtained. NMR and MS were consistent for the product.

EXAMPLES 2–6

In Examples 2–6, compounds were prepared as in Example 1 except that in Example 2 (15.2 g, 0.1 mol) methyl 4-hydroxybenzoate was used and S-2-methylbutyl bromide (15.1 g, 0.1 mol) was substituted for the S-4-methylhexyl bromide, in Example 3, methyl 3-chloro-4-hydroxybenzoate (5.6 g, 30 mmol) was substituted for the methyl 4-hydroxybenzoate and S-4-methylhexyl tosylate (8.1 g, 30 mmol) was substituted for the S-4-methylhexylbromide, in Example 4 methyl 3-methoxy-4-hydroxybenzoate (6.07 g, 33 mmol) was substituted for the methyl 4-hydroxybenzoate and S-4-methylhexyltosylate (9.0 g, 33 mmol) was substituted for the S-4-methylhexyl bromide in Example 5, (30.4 g, 0.1 mol) methyl-4-hydroxybenzoate was used and benzyl chloride (27.5 g, 0.22 mol) was substituted for the S-4-methylhexyl bromide, in Example 6, ( 3.04 g, 0.02 mol methyl-4-hydroxybenzogate was used and R-1-methylheptyl tosylate (5.68 g, 0.02 mol) was substituted for the S-4-methylhexyl bromide. The compounds thus-produced were S-4-(2-methylbutyloxy)benzoic acid (Example 2), S-3-chloro-4-(4-methylhexyloxy)benzoic acid (Example 3), S-3-methoxy-4-(4-methylhexyloxy)-benzoic acid (Example 4), 4-benzyloxybenzoic acid (Example 5), and S-4-(1′-methylheptyloxy)benzoic acid (Example 6).

EXAMPLE 7

Sodium hydride (1.2 g, 50 mmol) was suspended in 10 mL anhydrous tetrahydrofuran and S-2-methylbutanol (4.4 g, 50 mmol) was added dropwise. Upon completion of the addition, the reaction was stirred for 1 hour at room temperature. The solution was cooled to −78° C. and α-bromotolunitrile (9.8 g, 50 mmol) was added dropwise. The reaction was allowed to warm to room temperature and then refluxed for 1 day. The tetrahydrofuran was removed under reduced pressure and toluene added to the residue. This solution was washed 3 times with water, dried over anhydrous magnesium sulfate, filtered, and concentrated. The S-α-(2-methylbutyl)tolunitrile was vacuum distilled. This material was dissolved in 40 ml of methanol and 100 ml water containing 4 g NaOH and 4 g KOH was added. The resulting mixture was refluxed for 2 days and then acidified with 12N HCl. The precipitated S-α-(2-methylbutyl)toluic acid was collected by filtration and recrystallized from ethanol to give 9.8 g of product.

EXAMPLE 8

Sodium methylate was prepared by reacting sodium (0.58 g, 25 mol) with 25 ml anhydrous methanol. To the sodium methylate was added methyl 4-hydroxybenzoate (3.8 g, 25 mol). Excess methanol was removed under reduced pressure and toluene was added and removed under reduced pressure to remove any residual methanol. The solid residue was dissolved in 2:1 toluene-dimethyl formamide and 1,1-dihydroperfluorobutyl trifluoromethylsulfonate (8.3 g, 25 mmol) was added as a single portion and the mixture was refluxed for 1 day. The reaction product was cooled and washed 3 times with 100 ml water. The organic layer was dried over anhydrous $MgSO_4$, filtered, and concentrated. This crude methyl 4-(1,1-dihydroperfluorobutyloxy)benzoate was refluxed in 100 ml of 10% aqueous sodium hydroxide for day. The reaction product was cooled and acidified with concentrated aqueous HHCl. The precipated solid was collected by filtration and washed several times with cool water. This material was purified by recrystallization from ethanol-water. 4-(1,1-dihydroperfluorobutyloxy)benzoic acid (6.42 g, 80% yield) having a melting range of 182° to 183° C. was obtained.

EXAMPLES 9–15

In Examples 9, compounds were prepared as in Example 6 except that in Example 8 (3.8 g, 25 mmol) methyl 4-hydroxybenzoate was used and 1,1-dihydroperfluorohexyl trifluoromethylsulfonate (10.8 g, 25 mmol) was substituted for the 1,1-dihydroperfluorobutyl trifluoromethyl sulfonate, in Example 10 (3.8 g, 25 mmol) methyl 4-hydroxybenzoate was used and 1,1-dihydroperfluorooctyl trifluoromethylsulfonate (13.3 g, 25 mmol) was substituted for the 1,1-dihydroperfluorobutyl trifluoromethylsulfonate, in Example 11 (3.04 g, 20 mmol) methyl 4-hydroxybenzoate was used and 1,1,7-trihydroperfluoroheptyl trifluoromethylsulfonate (9.28 g, 20 mmol) was substituted for the 1,1-dihydroperfluorobutyl trifluoromethylsulfonate, in Example 12 methyl 3-chloro-4-hydroxybenzoate (2.79 g, 15 mmol) was substituted for the methyl 4-hydroxybenzoate and 1,1-dihydroperfluorohexyl trifluoromethylsulfonate (6.48 g, 15 mmol) was substituted for the 1,1-dihydroperfluorobutyl trifluoromethylsulfonate, in Example 13 1,1-dihydroperfluorohexyl trifluoromethylsulfonate (12.6 g, 30 mmol) was substituted for the 1,1-dihydroperfluorobutyl trifluoromethylsulfonate, and methyl 3-methoxy-4-hydroxybenzoate (5.46 g, 30 mmol was substituted for the methyl 4-hydroxybenzoate in Example 14, methyl 2-chloro-4-hydroxybenzoate (7.00 g, 0.0375 mol) was substituted for the methyl 4-hydroxybenzoate and 1,1-dihydroperfluorobutyl trifluoromethylsulfonate (13.28 g, 0.040 mol) was used, and in Example 15, methyl 2-chloro-4-hydroxybenzoate (1.87 g, 0.01 mol) was substituted for the methyl 4-hydroxybenzoate and 1,1-dihydroperfluorooctyl trifluoromethylsulfonate (5.32 g, 0.01 mol) was substituted for the 1,1-dihydroperfluorobutyl trifluoromethylsulfonate. The compounds thus-produced were 4-(1,1-dihydroperfluorohexyloxy)benzoic acid (Example 9), 4-(1,1-dihydroperfluorooctyloxy)benzoic acid (Example 10), 4-(1,1-7-trihydroperfluoroheptyloxy)benzoic acid (Example 11), 3-chloro-4-(1,1-dihydroperfluorohexyloxy)benzoic acid (Example 12), and 3-methoxy-4-(1,1-dihydroperfluorohexyloxy)benzoic acid (Example 13), 2-chloro-4-(1,1-hydroperfluorobutoxy)benzoic acid (Example 14), and 2-chloro-4-(1,1-dihydroperfluorooctyloxy)benzoic acid (Example 15).

EXAMPLE 16

Sodium methylate was prepared by reacting sodium (2.3 g, 0.1 mol) with 100 ml of anhydrous methanol. To the sodium methylate was added monotetrahydropyranylether of hydroquinone (19.4 g, 0.1 mol). Excess methanol was removed under reduced pressure and the residue was dissolved in 100 ml of 2:1 toluene-dimethylformamide. S-4-methylhexyl bromide (17.9 g, 0.1 mol) was added and the mixture was refluxed for 1 day. The reaction product was cooled and washed 4 times with 100 ml water and concentrated. The residue was treated with 100 ml 0.5 M HCl for 18 hours. Ether was added and the ethereal solution was washed 3 times with water, dried over anhydrous MgSO4, filtered and concentrated. The crude product was distilled and S-4-(4-methylhexyloxy)phenol (11.8 g, boiling range 142–145° C./0.8 mm) was obtained.

EXAMPLE 17

In Example 17 a compound was prepared as in Example 16 except that in Example 17 (48.5 g, 0.25 mol) monotetrahydropyranylether of hydroquinone was used and S-2-methylbutyl bromide (38 g, 0.25 mol) was substituted for the S-4-methylhexyl bromide. The thus-produced product was S-4-(2-methylbutyloxy)phenol.

EXAMPLE 18

Sodium hydride (0.12 g, 5 mmol) was suspended in 20 ml dimethylformamide. Monobenzylhydroquinone (1.0 g, 5 mmol) in 20 ml toluene was added. When the evolution of hydrogen ceased, 1-bromo-11-perfluorooctylundecane (2.37 g, 5 mmol) was added. The mixture was stirred and refluxed for 1 day. The reaction was cooled to room temperature and poured into 100 ml water, and extracted with ether. The ethereal extract was washed once With 1N sodium hydroxide, once with water, dried over anhydrous MgSO4, filtered, and concentrated. This crude intermediate was dissolved in 150 ml 2:1 anhydrous ethanol-ethyl acetate and hydrogenated using 0.6 g 10% palladium on carbon and a hydrogen pressure of 500 kPa at room temperature for 4 hours. The catalyst was removed by filtration and the solvents were removed under reduced pressure. The product, 1-(4-hydroxyphenoxy)-11-perfluorooctylundecane, weighed 2.6 g (76% yield).

EXAMPLES 19–20

In Examples 19–20 the compounds were prepared as in Example 18 except that in Example 19, (2.0 g, 10 mmol) of monobenzylhyaroquinone was used, and N-ethyl-N-(2-tosylethyl)perfluorooctylsulfonamide (7.31 g, 10 mmol) was substituted for 1-bromo-11-perfluorooctylundecane, and in Example 20, (10.0 g, 0.05 mol) monobenzylhydroquinone was used and R-1-methylheptyl tosylate (14.2 g, 0.05 mol was substituted for the 1-bromo-11-perfluorooctylundecane. The compounds thus-produced were N-ethyl-N-[(2-(4-hydroxyphenoxy)ethyl]perfluorooctylsulfonamide (Example 19) and S-4-(1-methylheptyloxy)phenol (Example 20).

EXAMPLE 21

Sodium hydride (5.0 g, 0.21 mol) was suspended in 150 ml dry glyme. Monobenzylhydroquinone (40 g, 0.20 mol) was dissolved in 500 ml anhydrous glyme and added dropwise to the sodium hydride with stirring under nitrogen atmosphere. Upon completion of the addition, the mixture was stirred at room temperature for 1 hour and then cooled to −78° C. 1,1-Dihydroperfluorobutyl trifluoromethylsulfonate (70.0 g, 0.21 mol) was then added dropwise and, upon completion of the addition, the reaction was allowed to warm slowly to room temperature. The glyme was removed under reduced pressure and 800 ml of water and 700 ml of ethyl ether were added to the residue and mixed vigorously. The ether layer was separated and washed twice with 5% sodium hydroxide, and twice with water, dried over anhydrous MgSO4, filtered and concentrated. A light orange-brown product (65 g) was obtained. This crude intermediate was dissolved in anhydrous ethanol and hydrogenated using 10% palladium on carbon and a hydrogen pressure of 500 kPa at room temperature for 2 hours. The catalyst was removed by filtration and the ethanol was removed under reduced pressure. The crude phenolic product was purified by high performance liquid chromatography (HPLC) using a prepacked 500 ml volume silica gel column and methylene chloride as eluent and recrystallization from petroleum ether. 4-(1,1-dihydroperfluorobutyloxy)phenol (34.63 g, 59.3% yield) was obtained.

EXAMPLES 22–28

In Examples 22–28, compounds were prepared as in Example 21 except that in Example 22 (20.0 g, 0.1 mol) monobenzylhydroquinone was used and 1,1-dihydroperfluorohexyl trifluoromethylsulfonate (45.0 g, 0.105 mol) was substituted for the 1,1-dihydroperfluorobutyl trifluoromethylsulfonate, in Example 23 (20.0 g, 100 mmol) monobenzylhydroquinone was used and 1,1-dihydroperfluorooctyl trifluoromethylsulfonate (58.5 g, 110 mmol) was substituted for the 1,1-dihydroperfluorobutyl trifluoromethylsulfonate, in Example 24 (10 g, 50 mmol) monobenzylhydroquinone was used and 1,1,2,2-tetrahydroperfluorohexyl trifluoromethylsulfonate 19.8 g, 50 mmol) was substituted for the 1,1-dihydroperfluorobutyl trifluoromethyl sulfonate, in Example 25 (3.5 g, 17.5 mmol) monobenzylhydroquinone was used and 1,1,7-trihydroperfluoroheptyl trifluoromethylsulfonate (8.1 g, 17.5 mmol) was substituted for the 1,1-dihydroperfluorobutyl trifluoromethylsulfonate, in Example 26 (4.0 g, 20 mmol) monobenzylhydroquinone was used and 1,1,11-trihydroperfluoroundecyl trifluoromethylsulfonate (3.66 g, 18.3 mmol) was substituted for the 1,1-dihydroperfluorobutyl trifluoromethylsulfonate, in Example 27 (3.66 g, 18.3.mmol) monobenzylhydroquinone was used and 2-(1,1-dihydroperfluorooctyloxy)ethyl trifluoromethylsulfonate (10.5 g, 18.3 mmol) was substituted for the 1,1-dihydroperfluorobutyl trifluoromethylsulfonate, and in Example 28 (20.0 g, 0.1 mol) monobenzylhydroquinone was used and 1,1-dihydroperfluoroethyl trifluoromethylsulfonate (23.2 g, 0.1 mol) was substituted for the 1,1-dihydroperfluorobutyltrifluoromethylsulfonate. The thus-produced products were 4-(1,1-dihydroperfluorohexyloxy)phenol (Example 22), 4-(1,1-dihydroperfluorooctyloxy)phenol (Example 23), 4-(1,1,2,2-tetrahydroperfluorohexyloxy)phenol (Example 24), 4-(1,1,7-trihydroperfluoroheptyloxy)phenol (Example 25), 4-(1,1,11-trihydroperfluoroundecyloxy)phenol (Example 26), 1-( 4-hydroxy-phenoxy-2-(1,1,-dihydroperfluorooctyloxy)ethane (Example 27), and 4-(1,1-dihydroperfluoroethoxy)phenol (Example 28).

EXAMPLE 29

4-Bromophenol (8.65 g, 0.05 mol) was dissolved in 25 ml dry glyme and added dropwise to a suspension of sodium hydride (1.2 g, 0.05 mol) in 25 ml anhydrous glyme. Upon completion of the addition, the mixture was stirred at room temperature for 30 minutes and 25 ml of dry dimethyl formamide was added. S-4-methylhexyl bromide (8.95 g, 0.05 mol) was then added and the mixture refluxed for 1 day. The reaction was filtered and the glyme removed under reduced pressure. Methylene chloride (50 ml) was added to the residue and this solution was washed once with water, once with 5% sodium hydroxide, and again with water, dried over anhydrous MgSO$_4$, filtered, and concentrated under reduced pressure. Distillation gave 12.1 g of S-1-bromo-4-(4methylhexyloxy)benzene having a boiling range of 158–163° C./9mm.

EXAMPLE 30

In Example 30, the procedure of Example 29 was followed except that (17.3 g, 0.1 mol) of 4-bromophenol was used and S-2-methyl butyl bromide (15.1 g, 0.1 mol) was substituted for the S-4-methylhexyl bromide to produce S-1-bromo-4-(2-methylbutyloxy)benzene.

EXAMPLE 31

Magnesium (2.66 g, 0.111 mol) was placed in a 250 ml flask and stirred without solvent for 15 minutes under dry nitrogen. Anhydrous tetrahydrofuran (THF) (100 ml) was then added to the flask. S-1-bromo-4-(4-methylhexyloxy)benzene (30.0 g, 0.111 mol) in 50 ml THF was placed in an addition funnel and 25% of this solution was run into the flask. This mixture was warmed carefully and when the reaction had begun, the heat was removed and the rate of reflux was controlled by the rate of addition of the remainder of the S-1-bromo-4-(4-methylhexyloxy)benzene solution. Upon completion of the addition, the reaction was refluxed for 2 hours, cooled to just below reflux and sulfur (3.4 g, 0.106 mol) was added very carefully in portions upon completion of the addition of the sulfur, the reaction was stirred at room temperature for 3 hours, filtered, and concentrated. Ethyl ether (200 ml) was added and 1M HCl was carefully added with vigorous stirring. The ether layer was separated and washed again with 1M HCl, washed once with water, dried over anhydrous MgSO$_4$, filtered, and concentrated. The crude product was distilled, yielding S-4-(4-methylhexyloxy)thiophenol (15.1 g, 63% yield) having a boiling range of 142–5° C./3 mm.

EXAMPLES 32–33

In Examples 32–33, the procedure of Example 31 was followed except that in Example 32 S-1-bromo-4-(2-methylbutyloxy)benzene (21.7 g, 0.089 mol) was substituted for the S-1-bromo-4-(4-methylhexyloxy)benzene to produce S-4-(2-methylbutyloxy)thiophenol and in Example 33 S-1-bromo-4-(2-methylbutoxy)benzene (2.67 g, 0.011 mol) was substituted for the S-1-bromo-4-(4-methylhexyloxy)benzene, and selenium (0.79 g, 0.010 mol) was substituted for the sulfur to produce S-4-(2-methylbutoxy)selenophenol.

EXAMPLE 34

Under a nitrogen atmosphere, chlorosulfonic acid (120 g, 1.03 mol) was cooled to −5° C. (+)-2-methylbutyl benzene (30 g, 0.20 mol) was added dropwise at a rate such that the temperature did not rise above 0° C. Upon completion of the addition, the reaction was stirred for 4 hours at 0° C. The solution was then carefully poured over 300 g of crushed ice. The resulting oil was washed with H$_2$O and then dissolved in a mixture of 130 ml concentrated sulfuric acid and 250 ml H$_2$O and cooled to −10° C. With vigorous stirring, 40 g of zinc was added in portions such that the temperature of the mixture did not rise above −5° C. The mixture was stirred at −5° C. for 30 minutes and allowed to warm to room temperature. The mixture was then warmed to 100° C. at which time an exotherm occurred. The mixture was maintained at 115° C. for 2 hours and then cooled to room temperature. The mixture was filtered to remove undissolved zinc and the filtrate was extracted 3 times with ether. The combined organics were dried over MgSO$_4$. The dessicant was removed by filtration and the ether removed on a rotary evaporator. The residue was distilled under reduced pressure and the S-4-(2-methylbutyl)thiophenol collected at 93–95° C. at 1.2 mm Hg.

EXAMPLE 35

Sodium methylate was prepared by reacting sodium (1.15 g, 50 mol) with 50 ml anhydrous methanol. To the sodium methylate was added 4-hydroxybenzaldehyde (6.1 g, 50 mmol). Excess methanol was removed under reduced pressure. The solid residue was dissolved in 2:1 toluene-dimethyl formamide and 1,1-dihydroperfluorohexyl trifluoromethylsulfonate (21.6 g, 50 mmol) was added all at once and the mixture refluxed for 1 day. The reaction was cooled and washed 3 times with 100 ml water. The organic layer was dried over anhydrous MgSO$_4$, filtered and concentrated. Distillation of this material produced 4-(1,1-dihydroperfluorohexyloxy)benzaldehyde (13.1 g, 65% yield) having a boiling range of 91–92° C./0.2 mm.

EXAMPLES 36–37

In Examples 36 and 37, compounds were prepared as in Example 35 except that in Example 36 1,1-dihydroperfluorobutyl trifluoromethylsulfonate (33.2 g, 100 mmol) was substituted for the 1,1-dihydroperfluorohexyl trifluoromethylsulfonate to produce 4-(1,1-dihydroperfluorobutyloxy)benzaldehyde and in Example 37 1,1-dihydroperfluorooctyl trifluoromethylsulfonate (13.3 g, 25 mmol) was substituted for the 1,1-dihydroperfluorohexyl trifluoromethylsulfonate to produce 4-(1,1-dihydroperfluorooctyloxy)benzaldehyde.

EXAMPLE 38

Sodium hydride (40 mmol) was suspended in anhydrous dimethyl formamide and 2,6-dihydroxynapthalene (20 mmol) was added upon completion of the evolution of hydrogen, S-4-methylhexyl tosylate (10 mmol) was added and the mixture refluxed for 1 day. The reaction product was acidified with aqueous HCl and extracted with ether. The ether extract was washed with water to remove the dimethyl formamide, dried over anhydrous MgSO$_4$, filtered, and concentrated. The crude product was purified by flash chromatography in 80:20 hexane:ethyl acetate on silica gel to yield S-6-(4-methylhexyloxy)-2-naphthol.

EXAMPLES 39 and 40

In Examples 39 and 40, compounds were prepared as in Example 38 except that in Example 39 1,4-dihydroxynaphthalene (20 mmol) was substituted for the 2,6-dihydroxynaphthalene to produce S-4-(4-methylhexyloxy)-1naphthol and in Example 40 1,5-dihydroxynaphthalene (20 mmol) was substituted for the 2,6-dihydroxynaphthalene to produce S-5-(4-methylhexyloxy)-1-naphthol.

EXAMPLE 41

To a suspension of sodium hydride (12 g, 0.3 mol, 60% in mineral oil) in 600 ml toluene and 400 ml dimethyl formamide was added 2,6-dihydroxynaphthalene (80 g, 0.5 mol) and the mixture was heated to reflux over a thirty minute period. Benzyl chloride (65 ml, 71.5 g, 0.56 mol) was added dropwise and the mixture was refluxed for 10 hours. After cooling to room temperature, the mixture was washed 6 times with water to remove the dimethyl formamide. The resulting toluene solution was washed twice with 150 ml 0.5N Sodium hydroxide to remove unreacted starting material and then with water and dried over anhydrous magnesium sulfate. The magnesium sulfate was removed by filtration and the filtrate was concentrated to 150 ml. The solid which had crystallized was collected by vacuum filtration and washed with a small amount of toluene to yield 2-benzyloxy-6-hydroxynaphthalene.

EXAMPLE 42

Sodium hydride (50 mmol) was suspended in 25 ml anhydrous diglyme and 2,6-dihydroxynapthalene (25 mmol) in 75 ml anhydrous diglyme was added. The mixture was warmed for 1 hour at 150° C., then cooled, and 1,1-dihydroperfluorobutyl trifluoromethylsulfonate (12.5 mmol) was added. The mixture was warmed for 2 days at 150° C., then cooled to room temperature. The reaction was acidified with 3M HCl and extracted twice with ether. The combined organic extractions were washed 4 times with water, dried over anhydrous MgSO$_4$, filtered, and concentrated. The crude material was purified by HPLC using methylene chloride on a silica gel-column to give 6-(1,1-dihydroperfluorobutyloxy)-2-napthol (1.9 g, 44% yield).

EXAMPLES 43–47

In Examples 43-47, compounds were prepared as in Example 42 except that in Example 43 1,4-dihydroxynaphthalene (3.2 g, 20 mmol) was substituted for the 2,6-dihydroxynaphthalene to produce 4-(1,1-dihydroperfluorobutyloxy)-1-naphthol, in Example 44 1,4-dihydroxynaphthalene (3.2 g, 20 mmol) was substituted for the 2,6-dihydroxynaphthalene and 1,1-dihydroperfluorohexyl trifluoromethylsulfonate (4.3 g, 10 mmol) was substituted for the 1,1-dihydroperfluorobutyl trifluoromethylsulfonate to produce 4-(1,1-dihydroperfluorohexyloxy)-1-naphthol, in Example 45 2,7-dihydroxynaphthalene (3.2 g, 20 mmol) was substituted for the 2,6-dihydroxynaphthalene to produce 7-(1,1-dihydroperfluorobutyloxy)-2-naphthol, in Example 46, 4,4'-biphenol was substituted for the 2,6-dihydroxynaphthalene and 1,1-dihydroperfluorooctyl trifluoromethylsulfonate was substituted for the 1,1-dihydroperfluorobutyltrifluoromethyl sulfonate to produce 4-(1,1-dihydroperfluorooctyloxy)-4'-hydroxybiphenyl, and in Example 47, 4,4'-biphenol was substituted for the 2,6-dihydroxynaphthalene to produce 4-(1,1-dihydroperfluorobutoxy)-4'-hydroxybiphenyl.

EXAMPLE 48

Sodium hydride (4.8 g, 0.2 mol) was suspended in 200 ml anhydrous glyme and S-4-methylhexanol (11.6 g, 0.1 mol) was added dropwise with stirring under nitrogen atmosphere at room temperature. Upon completion of the addition, 6-chloro-3-pyridine carboxylic acid (15.8 g, 0.1 mol) was added and this mixture was refluxed for 1 day. The reaction was acidified with 300 ml 0.5 M HCl and then extracted 3 times with ethyl ether. The combined ethereal extracts were then dried over anhydrous MgSO$_4$, filtered, and concentrated. The crude material was recrystallized from heptane twice to produce S-6-(4-methylhexyloxy)-3-pyridinecarboxylic acid (17.2 g, 73% yield) containing 8 weight percent of starting 6-chloro-3-pyridinecarboxylic acid by gas chromatography.

EXAMPLE 49–51

In Examples 49-51, compounds were prepared as in Example 48 except that in Example 49, S-2-methylbutanol (8.8 g, 0.10 mol) was substituted for the S-4-methylhexanol to produce S-6-(2-methylbutyloxy)-3-pyridinecarboxylic acid, in Example 50, S-1-methylheptanol (13.0 g, 0.1 mol ) was substituted for the S-4-methylhexanol to produce S-6-(1-methylheptyloxy)-3-pyridinecarboxylic acid and in Example 51, 1,1-dihydroperfluorobutanol (6.0 g, 0.03 mol) was substituted for the S-4-methylhexanol to produce 6-(1,1-dihydroperfluorobutyloxy )-3-pyridinecarboxylic acid.

EXAMPLES 52 AND 53

In Example 52, S-4-(2-methylbutyl )-4'-cyanobiphenyl (10 g) was hydrolyzed in methanol-water containing 8 g potassium hydroxide and 8 g sodium hydroxide for 7 days at reflux. The reaction was acidified with concentrated HCl and the product collected by filtration and dried under vacuum to produce S-4=(2-methylbutyl)-4'-biphenyl carboxylic acid. In Example 53, the procedure of Example 52 was followed except that S-4-(2-methylbutyloxy)-4'-cyanobiphenyl was substituted for the S-4-(2-methylbutyl)-4'-cyanobiphenyl to produce S-4-(2-methylbutyloxy)-4'-biphenyl carboxylic acid.

EXAMPLE 54

S-4-(4-methylhexyloxy)phenol (4.16 g, 0.02 mol) in 20 ml benzene was added dropwise at 25° C. under nitrogen atmosphere to a stirred suspension of sodium hydride (0.80 g, 0.02 mol, 60% in mineral oil) in 10 ml benzene. After completion of the addition, the mixture was refluxed for 1 hour and cooled to 25° C. 3,6-dichloropyridizine (2.98 g, 0.02 mol) in 20 ml benzene was added dropwise under nitrogen atmosphere at 25° C. with stirring. The resulting mixture was then refluxed for 12 hours. The reaction was cooled and toluene (50 ml) was added. The reaction mixture was then washed with water 3 times, dried over anhydrous magnesium sulfate, filtered and concentrated to give 5.50 g of S-3-chloro-6-[4'-(4''-methylhexyloxy)phenoxy]-pyridizine.

EXAMPLE 55

4-Benzyloxyphenol (10.0 g, 0.05 mol), 4-(1,1-dihydroperfluorobutoxy)benzoic acid (16.0 g, 0.05 mol) prepared as in Example 8, and 4-dimethylaminopyridine (0.1 g) were dissolved in 100 ml methylene chloride. Dicyclohexylcarbodiimide (11.0 g, 0.053 mol) was then added in one portion. The reaction mixture was stirred at 25° C. under nitrogen atmosphere for 12 hours. The reaction product was filtered, washed sequentially with 0.5N hydrochloric acid, 5% aqueous sodium bicarbonate, and water, dried over anhydrous magnesium sulfate, filtered, and concentrated to yield 22 g 4-benzyloxyphenyl 4'-(1,1rdihydroperfluorobutoxy)benzoate.

EXAMPLES 56-59

In Examples 56-59, the procedure of Example 55 was followed except that in Example 56 (1.6 g, 5 mmol) 4-(1,1-dihydroperfluorobutoxy)benzoic acid as used and 2-benzyloxy-6-naphthol (1.25 g, 5 mmol) was substituted for the 4-benzyloxyphenol, in Example 57, (2.0 g, 10 mmol) 4-benzyloxyphenol was used and S-4-methylhexanoic acid (1.30 g, 10 mmol) was substituted for the 4-(1,1-dihydroperfluorobutoxy)benzoic acid, in Example 58, 4-benzyloxybenzoic acid (2.28 g, 10 mmol) was substituted for the 4-(1,1-dihydroperfluorobutoxy)benzoic acid and 6-(1,1-dihydroperfluorobutoxy)-2-hydroxynaphthalene (3.42 g, 10 mmol) was substituted for the 4-benzyloxyphenol, in Example 59, 4-benzyloxybenzoic acid (2.28 g, 10 mmol) was substituted for the 4-(1,1-dihydroperfluorobutoxy)benzoic acid and 1,1-dihydroperfluorobutanol (2.00 g, 10 mmol) was substituted for the 4-benzyloxyphenol. The compounds thus-produces were 4-(1,1-dihydroperfluorobutoxy)benzoic acid 2'-(6'-benzyloxy)naphthyl ester (Example 56), S-4-benzyloxyphenyl 4-methylhexanoate (Example 57), 4-benzyloxybenzoic acid 2'-[6'-(1,1-dihydroperfluorobutoxy)]naphthyl ester (Example 58), and 1,1-dihydroperfluorobutyl 4-benzyloxybenzoate (Example 59).

EXAMPLE 60

4-Benzyloxyphenyl 4'-(1,1-dihydroperfluorobutoxy)-benzoate (22 g, 0.0438 mol) prepared as in Example 55, was dissolved in 50:50 by volume ethanol-ethyl acetate and hydrogenated at 60-65 psig hydrogen pressure over 2.0 g 10% palladium on carbon catalyst at 25° C. for 2 hours. The reaction solution was filtered to remove the catalyst and the solvent was removed under reduced pressure to yield 17.3 g 4-hydroxyphenyl 4'-(1''.1''-dihydroperfluorobutoxy)benzoate.

EXAMPLES 61-64

In Examples 61-64, the procedure of Example 60 was followed except the 4-benzyloxyphenyl 4'-(1'',1''-dihydroperfluorobutoxy)benzoate was not used and in Example 61 4-(1,1-dihydroperfluorobutoxy)benzoic acid 2'-(6'-benzyloxy)naphthyl ester was used, in Example 62 S-4-benzyloxyphenyl 4-methylhexanoate was used, in Example 63 4-benzyloxybenzoic acid 2'=[6'-(1,1-dihydroperfluorobutoxy)]naphthyl ester was used, and in Example 64, 1,1-dihydroperfluorobutyl 4-benzyloxybenzoate was used. The thus-produced compounds were 4-(1,1-dihydroperfluorobutoxy)benzoic acid 2'-(6'-hydroxy)naphthyl ester (Example 61), S-4-hydroxyphenyl 4-methylhexanoate (Example 62), 4-hydroxybenzoic acid 2'-[6'-(1,1-dihydroperfluorobutoxy)]-naphthyl ester (Example 63), and 1,1-dihydroperfluorobutyl 4-hydroxybenzoate. (Example 64).

EXAMPLE 65

Sodium (0.92 g, 40 mmol) was reacted with 40 ml anhydrous methanol. 4-Cyanophenol (4.76 g, 40 mmol) was added to this solution, the methanol was removed under pressure and the residue was dissolved in 100 ml 3:2 by volume toluene-dimethyl formamide. 1,1-Dihydroperfluorooctyl trifluoromethylsulfonate (21.28 g, 40 mmol) was then added dropwise at 25° C. and the resulting solution was refluxed for 12 hours. Water (100 ml) was added to the reaction mixture and the organic layer was washed with 10% aqueous sodium hydroxide and then with water. The organic phase was dried over anhydrous magnesium sulfate, filtered, and concentrated to yield 1-cyano-4-(1,1-dihydroperfluorooctyloxy)benzene.

EXAMPLE 66

1-Cyano-4-(1,1-dihydroperfluorooctyloxy) benzene was dissolved in 50 ml anhydrous ethanol and hydrogen chloride was bubbled through the solution at 25° C. under a nitrogen atmosphere for 3 hours. The reaction was allowed to stand for 4 days under nitrogen atmosphere and the resulting precipitate was quickly collected by filtration and transferred to a 250 ml round-bottomed flask containing 20 ml anhydrous ethanol under nitrogen atmosphere. Ammonia (50 ml, 9% in ethanol) was added and the solution was stirred for 2 days under nitrogen atmosphere. The resulting precipitated ammonium chloride was removed by filtration and the remaining solution was concentrated under reduced pressure. The resulting residue was recrystallized from 0.5N aqueous hydrochloride-ethanol to yield 6.15 g 4-(1,1-dihydroperfluorooctyloxy)benzamidine hydrochloride.

EXAMPLE 67

Sodium (0.70 g, 30 mmol) was reacted with 20 ml anhydrous methanol and then S-4-methylhexyl diethylmalonate (2.58 g, 10 mmol) was added followed by the addition of 4-(1,1-dihydroperfluorooctyloxy)benzamidine hydrochloride (5.54 g, 10 mmol). The resulting solution was refluxed for 3 days under nitrogen atmosphere, cooled to 25° C., and poured into 6N hydrochloric acid with stirring. The resulting precipitate was collected by filtration and dried under vacuum at 80° C. to yield 4.02 g S-2-[4-(1,1-dihydroperfluorooctyloxy)-phenyl]-4,6,-dihydroxy-5-(4-methylhexyl)pyrimidine.

EXAMPLE 68

S-2-[4-(1,1-dihydroperfluorooctyloxy)phenyl]-4,6,-dihydroxy-5-(4-methylhexyl)pyrimidine (4.00 g, 5.85 mmol) was reacted with 10 ml phosphorous oxychloride and 1.5 ml dimethylaniline at reflux under a nitrogen atmosphere for 2 days. The reaction mixture was cooled to 25° C. and the excess phosphorous oxychloride was removed under reduced pressure. The residue was poured into a mixture of 4 g sodium hydroxide and 50 g ice with stirring. This alkaline solution was extracted 4 times with ethyl ether and the combined ethereal extracts were washed twice with 6N hydrochloric acid, once with water, dried over anhydrous magnesium sulfate, filtered, and concentrated under reduced pressure. The resulting crude product was purified by HPLC using toluene and a silica gel column to yield 1.12 g S-4,6-dichloro-2-[4-(1,1-dihydroperfluorooctyloxy)phenyl]-5(4-methyl-hexyl)pyrimidine.

EXAMPLE 69

S-4-(2-methylbutyl)-4'-biphenylcarboxylic acid chloride (0.86 g, 3 mmol), derived from the carboxylic acid synthesized in Example 52, was added to a solution of 4-(1,1-dihydroperfluorohexyloxy)phenol (1.18 g, 3 mmol), synthesized in Example 22, in 30 ml dry ethyl ether containing 1 ml of dry triethylamine was added. The reaction was stirred for 1 day at room temperature at which time it was filtered, washed once with 0.5 M HCl, once with water, dried over anhydrous magnesium=sulfate, filtered, and concentrated under reduced pressure. The crude product was purified by HPLC (toluene, silica gel) followed by recrystallization from anhydrous ethanol to produce Compound 1, Table I, S-4-(2-methylbutyl)-4'-biphenylcarboxylic acid p'-(1,1-dihydroperfluorohexyloxy)phenyl ester (0.98 g, 51% yield). The structure was confirmed by H- and F-NMR, MS, and IR.

EXAMPLES 70–73

In Examples 70–73, compounds 2–5 of Table I were prepared as in Example 69 except that the precursor compounds indicated below were substituted for the S-2-(2-methylbutyl)-4'-biphenylcarboxylic acid chloride and the 4-(1,1-dihydroperfluorohexyloxy)phenol.

| Example | Compound | Precursors |
|---|---|---|
| 70 | 2 | S-4-(2-methylbutyl)-4'-biphenyl carboxylic acid (Example 52) and 4-(1,1-dihydroperfluorobutyloxy)phenol (Example 21) |
| 71 | 3 | S-4-(2-methylbutyl)-4'-biphenyl carboxylic acid (Example 52) and 4-(1,1-dihydroperfluorooctyloxy)phenol (Example 23) |
| 72 | 4 | S-4-(2-methylbutyloxy)-4'-biphenyl carboxylic acid (Example 53) and 1,1-dihydroperfluorooctanol |
| 73 | 5 | S-4-(2-methylbutyl)-4'-biphenyl carboxylic acid (Example 52) and 1,1-dihydroperfluorooctanol |

EXAMPLE 74

To a solution of S-4-(4-methylhexyloxy)thiophenol (1.12 g, B mmol), synthesized in Example 31 in 30 ml anhydrous ethyl ether containing i ml of dry triethylamine, 4-(1,1-dihydroperfluorohexyloxy)benzoic acid chloride (2.20 g, 5 mmol), derived from the material synthesized in Example 9, was added dropwise. The reaction was stirred for 1 day at room temperature at which time it was filtered, washed once with 0.5 M HCl, washed once with water, dried over anhydrous magnesium sulfate, filtered, and concentrated under reduced pressure. The crude product was purified by HPLC (toluene, silica gel) followed by recrystallization from anhydrous ethanol to produce Compound 6 of Table I, S-4-(1,1-dihydroperfluorohexyloxy)thiolbenzoic acid p'-(4-methylhexyloxy)phenyl ester (2.55g, 81% yield). The structure was confirmed by H- and F-NMR, MS, and IR.

EXAMPLES 75–80

In Examples 75–80, compounds 7–12 of Table I were prepared as in Example 74 except that the precursor compounds indicated below were substituted for the S-4-(4-methylhexyloxy)thiophenol and the 4-(1,1-dihydroperfluorohexyloxy)benzoic acid chloride.

| Example | Compound | Precursors |
|---|---|---|
| 75 | 7 | S-4-(2-methylbutyloxy)thiophenol (Example 32) and 4-(1,1-dihydroperfluorobutyloxy)benzoic acid (Example 8) |
| 76 | 8 | S-4-(4-methylhexyloxy)thiophenol (Example 31) and 4-(1,1-dihydroperfluorobutyloxy)benzoic acid (Example 8) |
| 77 | 9 | S-4-(2-methylbutyloxy)thiophenol (Example 32) and 4-(1,1-dihydroperfluorooctyloxy)benzoic acid (Example 10) |
| 78 | 10 | S-4-(4-methylhexyloxy)thiophenol (Example 31) and 4-(1,1-dihydroperfluorooctyloxy)benzoic acid (Example 10) |
| 79 | 11 | S-4-(2-methylbutyloxy)thiophenol (Example 32) and 4-(1,1-dihydroperfluorohexyloxy)benzoic acid (Example 9) |
| 80 | 12 | S-4-(2-methylbutyl)thiophenol (Example 34) and 4-(1,1-dihydroperfluorobutyloxy)benzoic acid (Example 8) |

EXAMPLE 81

S-4-(4-methylhexyloxy)benzoic acid (2.36 g, 10 mmol), synthesized in Example 1, and 4-(1,1-dihydroperfluorobutyloxy)phenol (2.92 g, 10 mmol), synthesized in Example 21, were dissolved in 50 ml methylene chloride. 6-(N,N-Dimethylamino)pyridine (0.1 g) was added to the reaction followed by N,N'-dicyclohexylcarbodiimide (2.27 g, 11 mmol). The reaction was stirred at room temperature under nitrogen atmosphere for 1 day. The reaction was filtered and washed successively with 0.5 M HHCl, 5% sodium bicarbonate, and water. The organic layer was dried over magnesium sulfate, filtered, and concentrated under reduced pressure. The crude material was purified by HPLC (toluene, silica gel) followed by recrystallization from ethanol to produce Compound 13 of Table I, S-4-(4-methylhexyloxy)benzoic acid p'-(1,1-dihydroperfluorobutyloxy)phenyl ester (3.84 g, 75% yield). The structure was confirmed by H- and F-NMR, MS, and IR.

EXAMPLES 82–114

In Examples 82–114, compounds 14–46 of Table I were prepared as in Example 81 except that the precursor compounds indicated below were substituted for the S-4-(4-methylhexyloxy)benzoic acid and the 4-(1,1,dihydroperfluorobutyloxy)phenol.

| Example | Compound | Precursors |
|---|---|---|
| 82 | 14 | S-4-(4-methylhexyloxy)benzoic acid (Example 1) and 1-(4-hydroxyphenoxy)-2-(1,1-dihydroperfluorooctyloxy)ethane (Example 27) |
| 83 | 15 | S-4-(2-methylbutoxy)phenol (Example 17) and 4-(1,1-dihydroperfluorohexyloxy)benzoic acid (Example 9) |
| 84 | 16 | S-4-(2-methylbutoxy)phenol (Example 17) and 4-(1,1-dihydroperfluorooctyloxy)benzoic acid (Example 10) |
| 85 | 17 | S-4-(4-methylhexyloxy)phenol (Example 16) and 4-(1,1-dihydroperfluorobutyloxy)benzoic acid (Example 8) |
| 86 | 18 | S-4-(4-methylhexyloxy)phenol (Example 16) and 4-(1,1-dihydroperfluorohexyloxy)benzoic acid (Example 9) |
| 87 | 19 | S-4(-methylhexyloxy)phenol (Example 16) and 4-(1,1-dihydroperfluorooctyloxy benzoic-acid (Example 10) |
| 88 | 20 | S-2-methylbutyl 4-hydroxybenzoate and 4-(1,1-dihydroperfluorobutyloxy)benzoic acid (Example 8) |
| 89 | 21 | S-4-(4-methylhexyloxy)benzoic acid (Example 1) and 4-(1,1-dihydroperfluorohexyloxy)phenol (Example 22) |
| 90 | 22 | S-4-(4-methylhexloxy)benzoic acid (Example 1) and 4-(1,1-dihydroperfluorooctyloxy)phenol (Example 23) |
| 91 | 23 | S-4-(4-methylhexyloxy)benzoic acid (Example 1) and 4-(1,1,2,2-tetrahydroperfluorohexyloxy)-phenol (Example 24) |
| 92 | 24 | S-4-(4-methylhexyloxy)benzoic acid (Example 1) and 4-(1,1,7-trihydroperfluoroheptyloxy)phenol (Example 25) |
| 93 | 25 | S-4-(2-methylbutyloxy)benzoic acid (Example 2) and 4-(1,1-dihydroperfluorooctyloxy)phenol (Example 23) |
| 94 | 26 | S-4-(2-methylbutyl)phenol and 4-(1,1-dihydroperfluorohexyloxy)benzoic acid (Example 9) |
| 95 | 27 | S-4-(2-methylbutyloxy)benzoic acid (Example 2) and 4-(1,1-dihydroperfluorohexyloxy)phenol (Example 22) |
| 96 | 28 | S-α-(2-methylbutyloxy)toluic acid (Example 7) and 4-(1,1-dihydroperfluorooctyloxy)phenol (Example 23) |
| 97 | 29 | S-4-(2-methylbutyloxy)phenol (Example 17) and 4-(1,1-dihydroperfluorobutyloxy)benzoic acid (Example 8) |
| 98 | 30 | S-4-(4-methylhexyloxy)benzoic acid(Example 1) and 1-(4-hydroxyphenoxy)-11-perfluorooctylundecane (Example 18) |
| 99 | 31 | S-3-chloro-4-(4-methylhexyloxy)benzoic acid (Example 3) and 4-(1,1-dihydroperfluorobutyloxy)phenol (Example 21) |
| 100 | 32 | S-3-chloro-4-(4-methylhexyloxy)benzoic acid (Example 3) and 4-(1,1-dihydroperfluorohexyloxy)phenol (Example 22) |
| 101 | 33 | S-4-(4-methylhexyloxy)phenol (Example 16 and 3-chloro-4-(1,1-dihydroperfluorohexyloxy)-benzoic acid (Example 12) |
| 102 | 34 | S-3-methoxy-4-(4-methylhexyloxy)benzoic acid (Example 4) and 4-(1,1-dihydroperfluorobutyloxy)phenol (Example 21) |
| 103 | 35 | S-3-methoxy-4-methylhexyloxy)benzoic acid (Example 4) and 4-(1,1-dihydroperfluorohexyloxy)phenol (Example 22) |
| 104 | 36 | S-4-(4-methylhexyloxy)phenol (Example 16) and 3-methoxy-4-(1,1-dihydroperfluorohexyloxy)benzoic acid (Example 13) |
| 105 | 37 | S-4-(4-methylhexyloxy)benzoic acid (Example 1) and N-ethyl-N-[2-(4-hydroxyphenoxy)ethyl]perfluorooctylsulfonamide (Example 19) |
| 106 | 38 | S-4-(4-methylhexyloxy)benzoic acid (Example 1) and 4-(1,1,11-trihydroperfluoroundecyloxy)-phenol (Example 26) |
| 107 | 39 | S-4-(4-methylhexyloxy)phenol (Example 16) and 4-(1,1,7-trihydroperfluoroheptyloxy)-benzoic acid (Example 11) |
| 108 | 40 | S-4-(4-methylhexyloxy)benzoic acid (Example 1) and 4-(1,1-dihydroperfluoroethoxy)phenol (Example 28). |
| 109 | 41 | S-4-)1-methylheptyloxy)benzoic acid (Example 6) and 4-(1,1-dihydroperfluorobutyloxy)phenol (Example 21) |
| 110 | 42 | S-4-)1-methylheptyloxy)benzoic acid (Example 6) and 4-(1,1-dihydroperfluorohexyloxy)phenol (Example 22) |
| 111 | 43 | S-4-)1-methylheptyloxy)benzoic acid (Example 6) and 4-(1,1-dihydroperfluorooctyloxy)phenol (Example 23) |
| 112 | 44 | S-4-(4-methylhexyloxy)phenol (Example 16) and 2-chloro 4-(1,1-dihydroperfluorobutyloxy)-benzoic acid (Example 14) |
| 113 | 45 | S-4-(4-methylhexyloxy)phenol (Example 16) and 2-chloro-4-(1,1-dihydroperfluorooctyloxy)-benzoic acid (Example 15) |
| 114 | 46 | S-4-(1-methylheptyloxy)phenol (Example 20) and 4-(1,1-dihydroperfluorobutyloxy)benzoic acid (Example 8) |

EXAMPLE 115

S-6-(4-methylhexyloxy)-3-pyridinecarboxylic acid (2.37 g, 10 mmol), synthesized in Example 48, and 4-(1,1-dihydroperfluorohexyloxy)phenol (3.92 g, 10 mmol), synthesized in Example 22, were dissolved in 50 ml methylene chloride. 4-(N,N-Dimethylamino)pyridine (0.1 g) was added to the reaction followed by N,N'-dicyclohexylcarbodiimide (2.27 g, 11 mmol). The reaction material was refluxed under a nitrogen atmosphere for 1 day. The reaction mixture was filtered and washed successively with 0.5 M HCl, 5% sodium bicarbonate, and water. The organic layer was dried over magnesium sulfate, filtered, and concentrated under reduced pressure. The crude material was purified by HPLC (toluene, silica gel) followed by recrystallization from heptane to produce Compound 47 of Table I, S-6-(4-methylhexyloxy)-3-pyridinecarboxylic acid p'-(1,1-dihydroperfluorohexyloxy)phenyl ester (2.90 g, 47% yield). The structure was confirmed by H- and F-NMR, MS, and IR.

EXAMPLES 116–121

In Examples 116–121, compounds 48–53 of Table I were prepared as in Example 115 except that the precursor compounds indicated below were substituted for the S-6-(4-methylhexyloxy)-3-pyridinecarboxylic acid and the 4-(1,1-dihydroperfluorohexyloxy)phenol.

| Example | Compound | Precursor |
|---|---|---|
| 116 | 48 | S-4-(4-methylhexyloxy)phenol (Example 16) and 6-(1,1-dihydroperfluorobutyloxy)-3-pyridinecarboxylic acid (Example 51) |
| 117 | 49 | S-6-(4-methylhexyloxy)-3-pyridine carboxylic acid (Example 48) and 4-(1,1-dihydroperfluorooctyloxy)phenol (Example 23) |
| 118 | 50 | S-6-(2-methylbutyloxy)-3-pyridine-carboxylic acid (Example 49) and 4-(1,1-dihydroperfluorohexyloxy)phenol (Example 22) |
| 119 | 51 | S-6-(4-methylhexyloxy)-3-pyridine-carboxylic acid (Example 48) and 4-(1,1-dihydroperfluorobutyloxy)phenol (Example 21) |
| 120 | 52 | S-6-(1-methylheptyloxy)-3-pyridine-carboxylic acid (Example 50) and 4-(1,1-dihydroperfluorobutyloxy)phenol (Example 21) |
| 121 | 53 | S-4-(4-methylhexyloxy)thiophenol (Example 31) and 6-(1,1-dihydroperfluorobutyloxy)-3-pyridinecarboxylic acid (Example 51) |

EXAMPLE 122

S-4-(4-methylhexyloxy)benzoic acid (0.71 g, 3 mmol), synthesized in Example 1, and 6-(1,1-dihydroperfluorobutyloxy)-2-napthol (1.03 g, 3 mmol), synthesized in Example 42, were dissolved in 50 ml methylene chloride. 4-(N,N-Dimethylamino)pyridine (0.03 g) was added to the reaction followed by N,N'-dicyclohexylcarbodiimide (1.03 g, 5 mmol). The reaction was stirred at room temperature under nitrogen atmosphere for 1 day. The reaction was filtered and washed successively with 0.5 M HHCl, 5% sodium bicarbonate, and water. The organic layer was dried over anhydrous magnesium sulfate, filtered, and concentrated under reduced pressure. The crude material was purified by HPLC (toluene, silica gel) followed by recrystallization from heptane to provide Compound 54 of Table I, S-4-(4-methylhexyloxy)benzoic acid 2'-(6'-(1,1-dihydroperfluorobutyloxy))naphthyl ester (0.60 g, 36% yield). The structure was confirmed by H- and F-NMR, MS, and IR.

EXAMPLES 123–128

In Examples 123–128 compounds 55–60 of Table I were prepared as in Example 122 except that the precursor compounds indicated below were substituted for S-6-(4-methylhexyloxy)benzoic acid and the 6-(1,1-dihydroperfluorobutyloxy)-2-naphthol.

| Example | Compound | Precursor |
|---|---|---|
| 123 | 55 | S-4-(4-methylhexyloxy)benzoic acid (Example 1) and 7-(1,1-dihydroperfluorobutyloxy)-2-naphthol (Example 45) |
| 124 | 56 | S-6-(4-methylhexyloxy)-2-naphthol (Example 38 and 4-(1,1-dihydroperfluorobutyloxy)benzoic acid (Example 8) |
| 125 | 57 | S-6-(4-methylhexyloxy)-2-naphthol (Example 38) and 4-(1,1-dihydroperfluorohexyloxy)benzoic acid (Example 9) |
| 126 | 58 | S-4-(4-methylhexyloxy)-1-naphthol (Example 39) and 4-(1,1-dihydroperfluorobutyloxy)benzoic acid (Example 8) |
| 127 | 59 | S-5-(4-methylhexyloxy)-1-naphthol (Example 40) and 4-(1,1-dihydroperfluorohexyloxy)benzoic acid (Example 9) |
| 128 | 60 | S-3-methoxy-4-(4-methylhexyloxy)benzoic acid (Example 4) and 6-(1,1-dihydroperfluorobutyloxy)-2-naphthol (Example 42) |

EXAMPLE 129

4-(1,1-Dihydroperfluorohexyloxy)benzaldehyde (2.02 g, 5 mmol), synthesized in Example 35, and S-4-(2-methylbutyl)aniline (0.82 g, 5 mmol) which was prepared as described in U.S. Pat. No. 4,394,070, which is incorporated herein by reference for that purpose, were dissolved in anhydrous ethanol and 1 drop of glacial acetic acid was added. The mixture was brought to reflux for 4 hours and allowed to cool to room temperature. The resulting product crystallized out of solution and was collected by filtration to provide compound 61 of Table 1, S-4-(1,1-dihydroperfluorohexyloxy)benzylidene-p'-(2-methylbutyl)aniline, (1.51 g, 55% yield). The structure was confirmed by H- and F-NMR, MS, and IR.

EXAMPLE 130

In Example 130 compound 62 of Table I was prepared as in Example 129 except that S-2-methylbutyl 4-aminobenzoate, the preparation of which is disclosed in European Patent Application No. 0,163,229 which is incorporated herein for that purpose, was substituted for the S-4-(2-methylbutylaniline).

EXAMPLE 131

S-4-(2'-Methylbutoxy)selenophenol (1.21 g, 0.005 mol) prepared as in Example 33, 4-(1',1'-dihydroperfluorobutoxy)benzoic acid (1.60 g, 0.005 mol), and 4-dimethylaminopyridine (0.05 g) were dissolved in 50 ml methylene chloride and to this solution was added dicyclohexylcarbodiimide (1.03 g, 0.005 mol). This reaction mixture was refluxed for 2 days under a nitrogen atmosphere. The reaction product was cooled to 25° C., filtered, washed sequentially with 0.5N hydrochloric acid, 5% aqueous sodium bicarbonate, and water, dried over anhydrous magnesium sulfate, filtered, and concentrated. This concentrate was purified by HPLC using toluene and a silica gel column to yield 0.3 g S-4-(2'-methylbutoxy)phenyl 4″(1‴,1‴-dihydroperfluorobutoxy)selenobenzoate (Compound 63).

EXAMPLE 132

1,1-Dihydroperfluorobutanol (2.00 g, 0.01 mol) was added to a stirred suspension of sodium hydride (0.40 g, 0.01 mol, 60% in mineral oil) in 20 ml benzene at 25° C. under a nitrogen atmosphere and the resulting mixture was stirred at 25° C. for 30 minutes. To this mixture S-3-chloro-6-[4'-(4″-methythexyloxy)phenoxy]pyridizine (3.2 g, 0.01 mol), prepared as in Example 54, in 30 ml benzene was added dropwise at 25° C. under a nitrogen atmosphere. After this addition, the reaction mixture was refluxed for 2 hours and then cooled to 25° C. Toluene (50 ml) was added the cooled reaction product which was then washed three times with water, dried over anhydrous magnesium sulfate, filtered, and concentrated. This concentrate was purified by HPLC using a silica column and toluene as eluent, followed by recrystallization from ethanol to yield Compound 64,S-3-(1',1'-dihydroperfluorobutoxy)-[4''-(methylhexyloxy)phenoxy]pyridizine.

EXAMPLE 133

4-Hydroxyphenyl 4'-(1,1,-dihydroperfluorobutoxy)-benzoate (2.06 g, 5 mmol), prepared as in Example 60. S-2-chloro-4-methylpentanoic acid (0.75 g, 5 mmol), and 4-dimethylaminopyridine (0.05 g) were dissolved in 50 ml methylene chloride. Dicyclohexylcarbodiimide (1.24 g, 6 mmol) was then added in a single portion. This reaction mixture was stirred at 25° C. under a nitrogen atmosphere for 12 hours. The reaction was filtered and then washed sequentially with 0.5N hydrochloric acid, 5% sodium bicarbonate, and water, dried over anhydrous magnesium sulfate, filtered, and concentrated. This concentrate was recrystallized from ethanol to yield 1.82 g S-4-(2'-chloro-4'-methylpentanoyloxy)phenyl 4''-(1,1-dihydroperfluorobutoxy)benzoate (Compound 65).

EXAMPLES 134–138

In Examples 134–138 compounds 66–70 of Table I were prepared as in Example 133 except that the precursor compounds set forth below were substituted for the 4-hydroxyphenyl 4'-(1,1-dihydroperfluorobutoxy)benzoate in Examples 134–136 and the precursor compounds set forth below were substituted for the 4-hydroxyphenyl 4'-(1,1-dihydroperfluorobutoxy)benzoate and the S-2-chloro-4-methylpentanoic acid in Examples 137–138.

| Example | Compound | Precursors |
|---|---|---|
| 134 | 66 | 4-(1,1-dihydroperfluorobutoxy)benzoic acid<br>2'-(6'-hydroxy)naphthyl ester (Example 61) |
| 135 | 67 | 4-hydroxybenzoic acid<br>2'-[6'-(1,1-dihydroperfluorobutoxy)]naphthyl ester (Example 63) |
| 136 | 68 | 4-(1,1-dihydroperfluorobutyloxy) 4'-hydroxybiphenyl (Example 46) |
| 137 | 69 | S-4-hydroxyphenyl 4-methylhexanoate (Example 62) and 4-(1,1-dihydroperfluorobutoxy)benzoic acid (Example 8) |
| 138 | 70 | 1,1-dihydroperfluorobutyl 4'-hydroxybenzoate (Example 64) and S-4-(methylhexyloxy) benzoic acid (Example 1) |

EXAMPLE 139

S-4,6-Dichloro-2-[4'-(1'',1''-dihydroperfluorooctyloxy)phenyl]-5-(4-methylhexyl)pyrimidine (100 mg, 0.14 mmol) was dissolved in 100 ml 1:1 by volume ethanol-ethyl acetate, 2 ml 1N sodium hydroxide was added, and the mixture was hydrogenated over 0.3 g 10% palladium on carbon catalyst at 60 psig hydrogen pressure for 30 minutes. The catalyst was removed by filtration and the filtrate was concentrated. This concentrate was dissolved in dichloromethane, dried over anhydrous magnesium sulfate, filtered, and concentrated to yield Compound 71, 2-[4-(1.1-dihydroperfluorooctyloxy)phenyl]-5-(4-methyl-hexyl)pyrimidine.

TABLE I

| No. | Compound |
|---|---|
| 1 | CH$_3$CH$_2$*CH(CH$_3$)—CH$_2$—⟨C$_6$H$_4$⟩—⟨C$_6$H$_4$⟩—C(=O)—O—⟨C$_6$H$_4$⟩—O—CH$_2$C$_5$F$_{11}$ |
| 2 | CH$_3$CH$_2$*CH(CH$_3$)—CH$_2$—⟨C$_6$H$_4$⟩—⟨C$_6$H$_4$⟩—C(=O)—O—⟨C$_6$H$_4$⟩—O—CH$_2$C$_3$F$_7$ |
| 3 | CH$_3$CH$_2$*CH(CH$_3$)—CH$_2$—⟨C$_6$H$_4$⟩—⟨C$_6$H$_4$⟩—C(=O)—O—⟨C$_6$H$_4$⟩—O—CH$_2$C$_7$F$_{15}$ |
| 4 | CH$_3$CH$_2$*CH(CH$_3$)—CH$_2$—O—⟨C$_6$H$_4$⟩—⟨C$_6$H$_4$⟩—C(=O)—O—CH$_2$C$_7$F$_{15}$ |
| 5 | CH$_3$CH$_2$*CH(CH$_3$)—CH$_2$—⟨C$_6$H$_4$⟩—⟨C$_6$H$_4$⟩—C(=O)—O—CH$_2$C$_7$F$_{15}$ |
| 6 | CH$_3$CH$_2$*CH(CH$_3$)—(CH$_2$)$_3$—O—⟨C$_6$H$_4$⟩—S—C(=O)—⟨C$_6$H$_4$⟩—O—CH$_2$C$_5$F$_{11}$ |

TABLE I-continued

| No. | Compound |
|---|---|
| 7 | CH₃CH₂C*H—CH₂—O—⟨Ph⟩—S—C(=O)—⟨Ph⟩—O—CH₂C₃F₇ <br> │ <br> CH₃ |
| 8 | CH₃CH₂C*H—(CH₂)₃—O—⟨Ph⟩—S—C(=O)—⟨Ph⟩—O—CH₂C₃F₇ <br> │ <br> CH₃ |
| 9 | CH₃CH₂C*H—CH₂—O—⟨Ph⟩—S—C(=O)—⟨Ph⟩—O—CH₂C₇F₁₅ <br> │ <br> CH₃ |
| 10 | CH₃CH₂C*H—(CH₂)₃—O—⟨Ph⟩—S—C(=O)—⟨Ph⟩—O—CH₂C₇F₁₅ <br> │ <br> CH₃ |
| 11 | CH₃CH₂C*H—CH₂—O—⟨Ph⟩—S—C(=O)—⟨Ph⟩—O—CH₂C₅F₁₁ <br> │ <br> CH₃ |
| 12 | CH₃CH₂C*HCH₂—⟨Ph⟩—S—C(=O)—⟨Ph⟩—O—CH₂C₃F₇ <br> │ <br> CH₃ |
| 13 | CH₃CH₂C*H—(CH₂)₃—O—⟨Ph⟩—C(=O)—O—⟨Ph⟩—O—CH₂C₃F₇ <br> │ <br> CH₃ |
| 14 | CH₃CH₂C*H—(CH₂)₃—O—⟨Ph⟩—C(=O)—O—⟨Ph⟩—O—(CH₂)₂—O—CH₂C₇F₁₅ <br> │ <br> CH₃ |
| 15 | CH₃CH₂C*H—CH₂—O—⟨Ph⟩—O—C(=O)—⟨Ph⟩—O—CH₂C₅F₁₁ <br> │ <br> CH₃ |
| 16 | CH₃CH₂C*H—CH₂—O—⟨Ph⟩—O—C(=O)—⟨Ph⟩—O—CH₂C₇F₁₅ <br> │ <br> CH₃ |
| 17 | CH₃CH₂C*H—(CH₂)₃—O—⟨Ph⟩—O—C(=O)—⟨Ph⟩—O—CH₂C₃F₇ <br> │ <br> CH₃ |
| 18 | CH₃CH₂C*H—(CH₂)₃—O—⟨Ph⟩—O—C(=O)—⟨Ph⟩—O—CH₂C₅F₁₁ <br> │ <br> CH₃ |
| 19 | CH₃CH₂C*H—(CH₂)₃—O—⟨Ph⟩—O—C(=O)—⟨Ph⟩—O—CH₂C₇F₁₅ <br> │ <br> CH₃ |

TABLE I-continued
| No. | Compound |
|---|---|
| 20 | 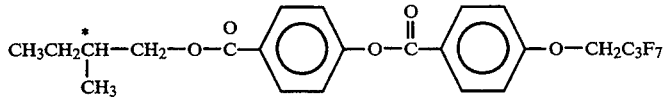 |
| 21 | 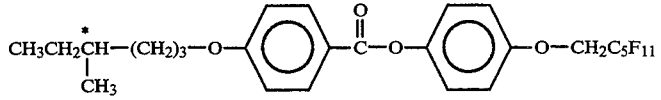 |
| 22 | 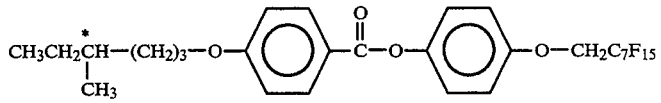 |
| 23 | 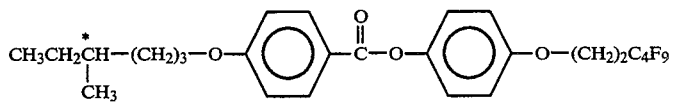 |
| 24 | 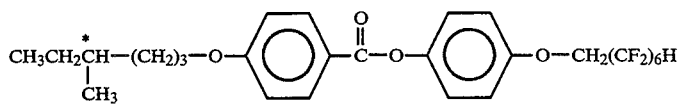 |
| 25 | 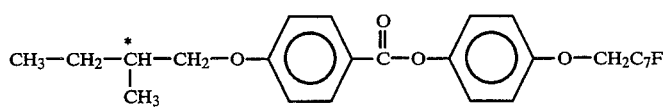 |
| 26 | 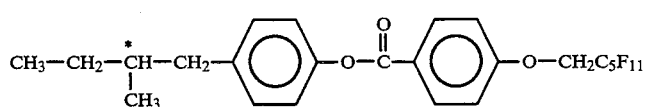 |
| 27 | 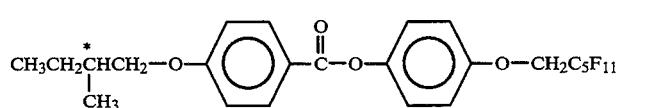 |
| 28 | 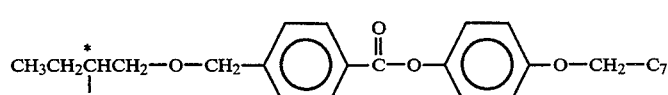 |
| 29 | 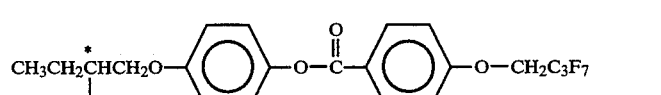 |
| 30 | 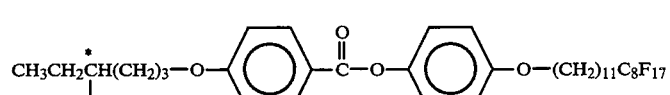 |
| 31 | 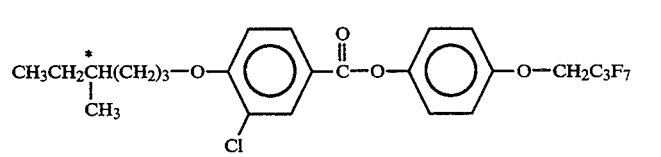 |

TABLE I-continued

| No. | Compound |
|---|---|
| 32 | CH$_3$CH$_2$*CH(CH$_2$)$_3$—O—[C$_6$H$_3$(Cl)]—C(=O)—O—[C$_6$H$_4$]—O—CH$_2$C$_5$F$_{11}$ (with CH$_3$ branch; Cl on first ring) |
| 33 | CH$_3$CH$_2$*CH(CH$_2$)$_3$—O—[C$_6$H$_4$]—C(=O)—O—[C$_6$H$_3$(Cl)]—O—CH$_2$C$_5$F$_{11}$ (with CH$_3$ branch; Cl on second ring) |
| 34 | CH$_3$CH$_2$*CH(CH$_2$)$_3$—O—[C$_6$H$_3$(O—CH$_3$)]—C(=O)—O—[C$_6$H$_4$]—O—CH$_2$C$_3$F$_7$ |
| 35 | CH$_3$CH$_2$*CH(CH$_2$)$_3$—O—[C$_6$H$_3$(O—CH$_3$)]—C(=O)—O—[C$_6$H$_4$]—O—CH$_2$C$_5$F$_{11}$ |
| 36 | CH$_3$CH$_2$*CH(CH$_2$)$_3$—O—[C$_6$H$_4$]—O—C(=O)—[C$_6$H$_3$(OCH$_3$)]—O—CH$_2$C$_5$F$_{11}$ |
| 37 | CH$_3$CH$_2$*CH(CH$_2$)$_3$—O—[C$_6$H$_4$]—C(=O)—O—[C$_6$H$_4$]—OCH$_2$CH$_2$N(CH$_2$CH$_3$)SO$_2$C$_8$F$_{17}$ |
| 38 | CH$_3$CH$_2$*CH(CH$_2$)$_3$—O—[C$_6$H$_4$]—C(=O)—O—[C$_6$H$_4$]—O—CH$_2$(CF$_2$)$_{10}$H |
| 39 | CH$_3$CH$_2$*CH(CH$_2$)$_3$—O—[C$_6$H$_4$]—O—C(=O)—[C$_6$H$_4$]—O—CH$_2$(CF$_2$)$_6$H |
| 40 | CH$_3$CH$_2$*CH(CH$_2$)$_3$O—[C$_6$H$_4$]—C(=O)—O—[C$_6$H$_4$]—OCH$_2$CF$_3$ |
| 41 | C$_6$H$_{13}$*CH(CH$_3$)O—[C$_6$H$_4$]—C(=O)—O—[C$_6$H$_4$]—OCH$_2$C$_3$F$_7$ |
| 42 | C$_6$H$_{13}$*CH(CH$_3$)O—[C$_6$H$_4$]—C(=O)—O—[C$_6$H$_4$]—OCH$_2$C$_5$F$_{11}$ |
| 43 | C$_6$H$_{13}$*CH(CH$_3$)O—[C$_6$H$_4$]—C(=O)—O—[C$_6$H$_4$]—OCH$_2$C$_7$F$_{15}$ |

TABLE I-continued
| No. | Compound |
|---|---|
| 44 | 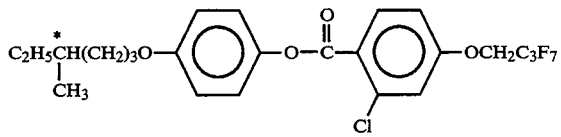 |
| 45 | 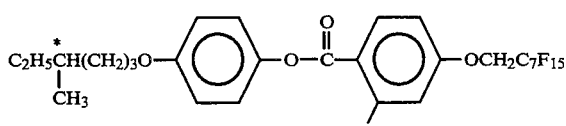 |
| 46 | 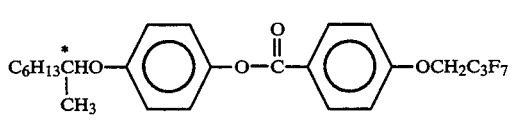 |
| 47 | 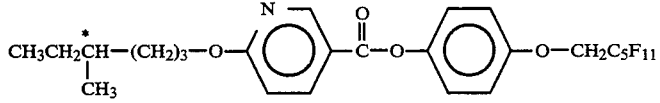 |
| 48 | 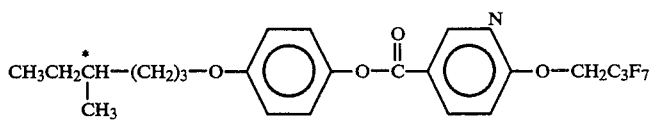 |
| 49 | 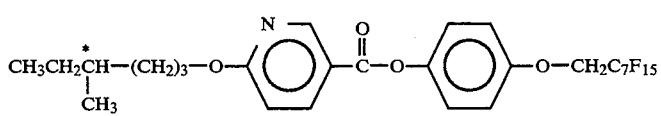 |
| 50 | 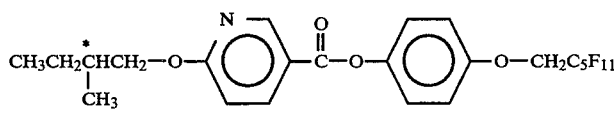 |
| 51 | 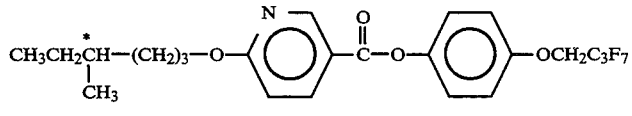 |
| 52 | 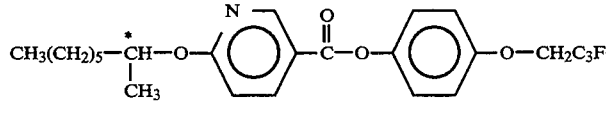 |
| 53 | 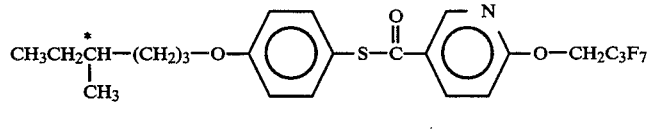 |
| 54 | 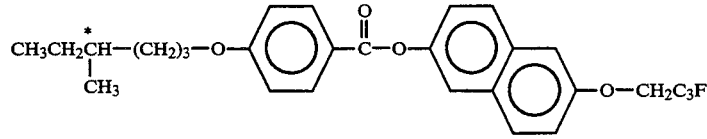 |

TABLE I-continued

| No. | Compound |
|---|---|
| 55 | CH₃CH₂C*H(CH₂)₃—O—⟨Ph⟩—C(=O)—O—⟨Naph⟩—O—CH₂C₃F₇ (with CH₃ on chiral carbon) |
| 56 | CH₃CH₂C*H(CH₂)₃—O—⟨Naph⟩—O—C(=O)—⟨Ph⟩—O—CH₂C₃F₇ (with CH₃ on chiral carbon) |
| 57 | CH₃CH₂C*H(CH₂)₃—O—⟨Naph⟩—O—C(=O)—⟨Ph⟩—O—CH₂C₅F₁₁ (with CH₃ on chiral carbon) |
| 58 | CH₃CH₂C*H(CH₂)₃—O—⟨Naph⟩—O—C(=O)—⟨Ph⟩—O—CH₂C₃F₇ (with CH₃ on chiral carbon) |
| 59 | CH₃CH₂C*H(CH₂)₃—O—⟨Naph⟩—O—C(=O)—⟨Ph⟩—O—CH₂C₅F₁₁ (with CH₃ on chiral carbon) |
| 60 | CH₃CH₂C*H(CH₂)₃—O—⟨Ph(OCH₃)⟩—C(=O)—O—⟨Naph⟩—OCH₂C₃F₇ (with CH₃ on chiral carbon) |
| 61 | CH₃CH₂C*HCH₂—⟨Ph⟩—N=CH—⟨Ph⟩—O—CH₂C₅F₁₁ (with CH₃ on chiral carbon) |
| 62 | CH₃CH₂C*H—CH₂—O—C(=O)—⟨Ph⟩—N=CH—⟨Ph⟩—O—CH₂—C₅F₁₁ (with CH₃ on chiral carbon) |
| 63 | C₂H₅C*HCH₂O—⟨Ph⟩—Se—C(=O)—⟨Ph⟩—OCH₂C₃F₇ (with CH₃ on chiral carbon) |
| 64 | C₂H₅C*H(CH₂)₃O—⟨Ph⟩—O—⟨pyridazine N=N⟩—OCH₂C₃F₇ (with CH₃ on chiral carbon) |

TABLE I-continued

| No. | Compound |
|---|---|
| 65 | CH₃CHCH₂CHC(O)-[phenyl]-O-C(O)-[phenyl]-OCH₂C₃F₇ (with CH₃ and Cl substituents, * chiral center) |
| 66 | CH₃CHCH₂CHC(O)-[naphthyl]-O-C(O)-[phenyl]-OCH₂C₃F₇ (with CH₃ and Cl substituents, * chiral center) |
| 67 | CH₃CHCH₂CHC(O)-[phenyl]-C(O)-O-[naphthyl]-OCH₂C₃F₇ (with CH₃ and Cl substituents, * chiral center) |
| 68 | CH₃CHCH₂CHC(O)-[phenyl]-[phenyl]-OCH₂C₇F₁₅ (with CH₃ and Cl substituents, * chiral center) |
| 69 | C₂H₅CH(CH₂)₂CO-[phenyl]-O-C(O)-[phenyl]-OCH₂C₃F₇ (with CH₃ substituent, * chiral center) |
| 70 | CH₃CH₂CH(CH₂)₃O-[phenyl]-C(O)-O-[phenyl]-C(O)-OCH₂C₃F₇ (with CH₃ substituent, * chiral center) |
| 71 | C₂H₅CH(CH₂)₃-[pyrimidine]-[phenyl]-OCH₂C₇F₁₅ (with CH₃ substituent, * chiral center) |

Compounds in Table I were evaluated for transition temperatures, birefringence, and pitch length using the following procedures:

Transition temperature determinations were made either by optical observation of material phase changes using a Mettler FP-5 hot stage and a Leitz polarizing microscope, or by standard practice differential scanning calorimetry (DSC) using a Perkin Elmer model DSC-4.

Birefringence of the C* phase was measured using a wedged technique as described in *Japanese Journal of Applied Physics*, Vol. 24, No. 11, Nov. 1985, p. 1389–1393.

Pitch length was measured by optical microscopy as described in *Journal de Physique Colloq.*, Vol. 37, 1976, p. C3-129-132, except that 50–75 micron thick cells were used.

Transition temperatures, birefringence and pitch length are reported in Table II.

Where the material melts during the K→I transition, the notation "mp" for melting point follows the melt temperature. Birefringence and pitch length measurements are not reported in Table II for materials that either do not show a chiral smectic C phase themselves or whose phase is observed only upon rapid cooling and therefore cannot be measured.

TABLE II

| Cmpd | Transition Temp (°C.) I → A | A → C* | C* → K | Birefringence (Δn) | Pitch length (microns) |
|---|---|---|---|---|---|
| 1 | 210 | 82 | 78 | — | — |
| 2 | 188 | 100 | 94 | .16(98°C.) | 5.7 |
| 3 | 231 | — | (A → K)93 | — | — |
| 4 | 115 | 96(H*) | — | — | — |
| 5 | 101 | — | (A → K)72 | — | — |
| 6 | 108 | 93 | 49 | .12(81° C.) | 5.1 |
| 7 | 82 | 76 | 71 | .14(75° C.) | 3.0 |
| 8 | 86 | 60 | — | .13(54° C.) | 3.3 |
| 9 | 125 | — | (A → K)97 | — | — |
| 10 | 132 | 95 | 74 | .09(82° C.) | 13.9 |
| 11 | 98 | 85 | 63 | .12(78° C.) | 7.0 |
| 12 | 68mp | — | — | — | — |
| 13 | 76 | 60 | 40 | .12(56° C.) | 6.0 |
| 14 | 91 | 72 | 51 | — | — |
| 15 | 83 | 61 | — | .10(58° C.) | 6.6 |
| 16 | 110 | 81 | 66 | — | — |
| 17 | 74 | 60 | 57 | — | — |
| 18 | 89 | 78 | 52 | .11(55° C.) | 6.0 |
| 19 | 109 | 81 | 78 | .09(79° C.) | 6.7 |
| 20 | 101mp | — | — | — | — |
| 21 | 96 | 62 | 23ᵃ | .11(53° C.) | 7.4 |
| 22 | 124 | 65 | 54ᵇ | .10(59° C.) | 9.8 |
| 23 | 104 | 75 | 47 | .10(73° C.) | 7.3 |
| 24 | 48 | — | (A → K)30 | — | — |
| 25 | 116 | — | (A → K)51 | — | — |
| 26 | 68mp | — | — | — | — |
| 27 | 85 | — | (A → K)40 | — | — |

TABLE II-continued

| Cmpd | Transition Temp (°C.) I → A | A → C* | C* → K | Birefringence (Δn) | Pitch length (microns) |
|---|---|---|---|---|---|
| 28 | 78 | — | (A → K)53 | — | — |
| 29 | 86mp | — | — | — | — |
| 30 | 122 | 90 | 85 | .07(99° C.) | 20.0 |
| 31 | 57 | — | (A → K)55 | — | — |
| 32 | 84 | — | (A → K)28 | — | — |
| 33 | 63 | 41 | 35 | .08(40° C.) | 2.0 |
| 34 | 70mp | — | — | — | — |
| 35 | 59 | — | (A → K)40 | — | — |
| 36 | 42 | — | (A → K)28 | — | — |
| 37 | 113 | — | (A → K)78 | — | — |
| 38 | 97 | — | (A → K)91 | — | — |
| 39 | 61mp | — | — | — | — |
| 40 | 69 | — | (A → K)35 | — | — |
| 41 | 41mp | — | — | — | — |
| 42 | 18 (I → K) | — | — | — | — |
| 43 | 40 | 21 | (A → H*) | — | — |
| 44 | liquid | — | — | — | — |
| 45 | 71 | — | (A → K)37 | — | — |
| 46 | 37mp | — | — | — | — |
| 47 | 62 | 33 | — | .10(31° C.) | 5.8 |
| 48 | 49 | 28 | 22 | — | — |
| 49 | 88 | 54 | 51 | — | — |
| 50 | 54mp | — | — | — | — |
| 51 | 48 | — | (A → K)30 | — | — |
| 52 | 35mp | — | — | — | — |
| 53 | 75 | 32 | 28 | — | — |
| 54 | 124 | 83 | 69 | .14(80° C.) | 6.6 |
| 55 | 98mp | — | — | — | — |
| 56 | 119 | 62 | 47 | .14(58° C.) | 4.2 |
| 57 | 151 | 96 | 63 | .12(94° C.) | 6.9 |
| 58 | 85mp | — | — | — | — |
| 59 | 80 | 37 | — | .06(36° C.) | 6.0 |
| 60 | 93mp | — | — | — | — |
| 61 | 76 | — | (A → K)60 | — | — |
| 62 | 118 | — | (A → K)83 | — | — |
| 63 | 73 | — | (A → K)66 | — | — |
| 64 | 68 (I → K) | — | — | — | — |
| 65 | 41 | — | (A → K)40 | — | — |
| 66 | 131 | — | (A → K)125 | — | — |
| 67 | 110 | — | (A → K)90 | — | — |
| 68 | 98 | — | (A → K)88 | — | — |
| 69 | 86 | 72 | 65 | — | — |
| 70 | 70 | 60 | 25 | — | — |
| 71 | 72mp | — | — | — | — |

[a] on cooling an additional peak was observed by DSC at 25° C.
[b] on cooling an additional peak was observed by DSC at 56° C.

EXAMPLES 140–168

Binary mixtures were made of compounds which of themselves did not exhibit a chiral smectic mesophase. Equal weight amounts of materials were placed next to each other on a clean glass microscope slide and covered with a clean glass cover slip. This preparation was warmed over a bunsen burner until both materials were isotropic at which point a continuous composition gradient was formed between the two components. The slide was then placed on a microscope between crossed polarizers, allowed to cool, and the mesophases present were identified. The compounds mixed as components 1 and 2 of the binary mixtures and the observed mesophases are set forth in Table III.

TABLE III

| Example | Compound No. for Component 1 | Compound No. for Component 2 | Observed mesophases |
|---|---|---|---|
| 140 | 20 | 29 | A,C* |
| 141 | 27 | 29 | A,C* |
| 142 | 20 | 27 | A,C* |
| 143 | 27 | 50 | A,C* |
| 144 | 50 | 51 | A,C* |
| 145 | 20 | 26 | A,C* |
| 146 | 25 | 28 | A,H* |
| 147 | 20 | 24 | A,C* |
| 148 | 27 | 24 | A,C* |
| 149 | 36 | 37 | A,C* |
| 150 | 55 | 32 | A,C* |
| 151 | 29 | 32 | A,C*,H* |
| 152 | 30 | 36 | A,C* |
| 153 | 34 | 36 | A,C* |
| 154 | 35 | 61 | A,C* |
| 155 | 34 | 62 | A,C* |
| 156 | 50 | 52 | A,C* |
| 157 | 29 | 31 | A,C* |
| 158 | 12 | 20 | A,C* |
| 159 | 24 | 40 | A,C* |
| 160 | 71 | 20 | A,H* |
| 161 | 41 | 37 | A,H* |
| 162 | 43 | 32 | A,C*,H* |
| 163 | 44 | 32 | A,C* |
| 164 | 45 | 32 | A,C* |
| 165 | 42 | 51 | A,C* |
| 166 | 63 | 27 | A,C* |
| 167 | 46 | 51 | A,C* |
| 168 | 68 | 20 | A,C* |

EXAMPLE 169

Admixtures of Compound No. 20 and Compound No. 29 were prepared at various mixing ratios as set forth in Table IV. Transition temperatures for the admixtures, as well as for each individual compound are set forth in Table IV.

TABLE IV

| Compound 20 (wt %) | Compound 29 (wt %) | Transition temperature (°C.) | | | |
|---|---|---|---|---|---|
| | | I → A | A → C* | C → K* | I → K |
| 100 | 0 | — | — | — | 88 |
| 59 | 41 | 64.9 | 58.5 | 56.3 | |
| 49 | 51 | 64.3 | 57.5 | 56.3 | |
| 39 | 61 | 63.6 | 62.7 | 62.3 | |
| 0 | 100 | — | — | — | 79 |

EXAMPLE 170

A device utilizing ferroelectric liquid crystal materials of this invention was constructed as follows. A 600 Å thick indium tin oxide pattern of 25 lines, 700 micrometers wide and spaced 300 micrometers apart, was deposited on two 60 mm by 70 mm Corning 7104 glass plates.

One plate was further coated with photoresist, exposed through a circular holed mask and developed resulting in photoresist posts approximately 1.7 microns in height, 200 microns in diameter and spaced 5 mm apart. These posts serve as spacers for the assembled device determining the liquid crystal fill gap between the plates.

Both plates were further coated with DuPont VK6300 polyimide and undirectionally buffed with a buffing pad, imparting order to the polymer layer which then serves to uniaxially align the enclosed liquid crystal.

The line patterns of the two plates were then aligned 90° to each other forming a 25×25 pixel array. The plates were sealed around their edges with Norland UV sealant #UVS-91. This construction was then filled in a vacuum chamber with the following mixture:

23.3% of compound number 13,
27.4% of-compound number 21,
46.1% of S-2methylbutyl-4-(4'-octyloxybenzoyloxy)-benzoate, and
3.2% of S-4-hexyloxyphenyl-4'-[4''(4'''-methylhexyloxy)benzoyloxy]benzoate.

The last two compounds are described in "Some Novel Ferroelectric Smectic Liquid Crystals" by J. W. Goodby and T. M. Leslie in Liquid Crystals and Ordered Fluids Vol. 4, pp 1–42, edited by A. C. Griffin and J. F. Johnson. The mixture, when evaluated at room temperature had a pitch length of 3.0–4.0 microns, a tilt angle of 27° and a birefringence of 0.15, transition temperatures for phase changes were 76° C.(I→A) and 45° C.(A→C*).

The filled device was heated to 74° C. to the isotropic phase of the liquid crystal mixture and allowed to cool. As the material cooled from its isotropic..phase to its A phase, the molecules were spontaneously oriented by the buffed polymer surfaces. The liquid crystal maintains this alignment on further cooling to room temperature.

Electrical driving circuitry was connected to the indium tin oxide lines. Application of ±40 volts across any pixel resulted in the liquid crystal mixture switching with a response time of 110 microseconds.

EXAMPLE 171

A mixture of ferroelectric liquid crystal compounds was prepared using

| | |
|---|---|
| S-4-(4-methylhexyloxy)benzoic acid p'-(1,1-dihydroperfluorobutyloxy)-phenyl ester (Compound 13) | 30 wt. % |
| S-4-(4-methylhexyloxy)benzoic acid p'-(1,1-dihydroperfluorohexyloxy)-phenyl ester (Compound 21) | 19 wt. % |
| S-4-(2'-chloro-4'-methylpentanoyloxy)-phenyl 4''-(1,1-dihydroperfluorobutoxy)-benzoate (Compound 65) | 11 wt. % |
| S-2-methylbutyl 4-(4'-octyloxybenzoyloxy)benzoate (Goodby and Leslie, supra) | 40 wt % |

The transition temperatures for the mixture were
I →A 69° C.
A →C* 49° C.
C*→K 0° C.

A device prepared as in Example 170, was vacuum filled as in Example 170. The response time was measured at the rising edge of the cell photoresponse and calculated from 10–90% of the maximum transmission. The response time, measured at a voltage of ±30 and a temperature of 23° C., was 69 μs. The polarization, determined at 23° C. according to the procedure of Miyasato et al., Jap. J. Appl. Phys., 22, 1983, p. 661, was 22 nC/cm².

EXAMPLES 172–175

For Examples 172–175, ferroelectric liquid crystal mixtures were prepared and tested as in Example 171. The mixtures, as well as the transition temperatures, response times and polarization for the mixtures, were as follows:

Example 172:

| | |
|---|---|
| S-4-(4-methylhexyloxy)benzoic acid p'-(1,1-dihydroperfluorobutyloxy)-phenyl ester (Compound 13) | 31 wt. % |
| S-4-(4-methylhexyloxy)benzoic acid p'-(1,1-dihydroperfluorohexyloxy)-phenyl ester (Compound 21) | 19 wt. % |
| S-4-(2'-chloro-4'-methylpentanoyloxy)-phenyl 4''-(1,1-dihydroperfluorobutoxy)-benzoate (Compound 65) | 20 wt. % |
| S-2-methylbutyl-4-(4'-octyloxybenzoyloxy)benzoate (Goodby and Leslie, supra) | 30 wt % |

The transition temperatures for the mixture were
I→A 69° C.
A →C, 50° C.
C*→K 8° C.

The response time at a voltage of ±30 and a temperature of 23° C. was 39 μs. The response time at a voltage of ±40 and a temperature of 40° C. was 19 μs. The polarization at 23° C. was 39 nC/cm².

Example 173:

| | |
|---|---|
| S-4-(4-methylhexyloxy)benzoic acid p'-(1,1-dihydroperfluorobutyloxy)-phenyl ester (Compound 13) | 30 wt. % |
| S-4-(4-methylhexyloxy)benzoic acid p'-(1,1-dihydroperfluorohexyloxy)-phenyl ester (Compound 21) | 20 wt. % |
| S-4-(2'-chloro-4'-methylpentanoyloxy)-phenyl 4''-(1,1-dihydroperfluorobutoxy)-benzoate (Compound 65) | 20 wt. % |
| S-1,1-dihydroperfluorobutyl 4-[4'-(4''-methylhexyloxy)benzoyloxy]benzoate (Compound 70) | 30 wt. % |

The transition temperatures for the mixture were
I→A 72° C.
A→C* 53° C.
C*→K 8° C.

The response time at voltage of ±30 and a temperature of 26° C. was 59 μs. The polarization at 26° C. was 37 nC/cm².

Example 174:

| | |
|---|---|
| S-4-(1,1-dihydroperfluorohexyloxy)-thiolbenzoic acid p'-(4-methylhexyloxy)phenyl ester (Compound 6) | 19 wt. % |
| S-4-(4-methylhexyloxy)benzoic acid p'-(1,1-dihydroperfluorobutyloxy)-phenyl ester (Compound 13) | 20 wt. % |
| S-4-(4-methylhexyloxy)benzoic acid p'-(1,1-dihydroperfluorohexyloxy)-phenyl ester (Compound 21) | 23 wt. % |
| S-4-(2'-chloro-4'-methylpentanoyloxy)-phenyl 4''-(1,1-dihydroperfluorobutoxy)-benzoate (Compound 65) | 19 wt. % |
| S-2-methylbutyl 4-(4'-octyloxybenzoyloxy)benzoate (Goodby and Leslie, supra) | 20 wt % |

The transition temperatures for the mixture were
I→A 81° C.
A→C* 58° C.
C*→K 23° C.

The response time at a voltage of ±30 and a temperature of 32° C. was 11 μs. The polarization at a temperature of 32° C. was 30 nC/cm².

Example 175:

| | |
|---|---|
| S-4-(4-methylhexyloxy)benzoic acid p'-(1,1-dihydroperfluorohexyloxy)-phenyl ester (Compound 21) | 50 wt. % |
| S-4-(2'-chloro-4'-methylpentanoyloxy)-phenyl 4''-(1,1-dihydroperfluorobutoxy)- | 50 wt. % |

| -continued |
|---|
| benzoate (Compound 65) |

The transition temperatures for the mixture were

I →A 79° C.

A →C* 48° C.

The response time at a voltage of ±40 and a temperature of 42° C. was 12 μs. The polarization at 42° C. was 75.5 nC/cm².

The various modifications and alterations of this invention will be apparent to those skilled in the art without departing from the scope and spirit of this invention and this invention should not be restricted to that set forth herein for illustrative purposes.

What is claimed is:

1. A compound represented by the formula

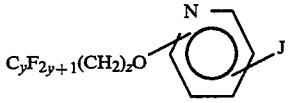

where J is —COOH or —CHO, y is 1 to 20, and Z is 1 to 20.

2. The compound 6-(1,1-dihydroprfluorobutyloxy)-3-pyridinecarboxylic acid.

* * * * *

UNITED STATES PATENT AND TRADEMARK OFFICE
CERTIFICATE OF CORRECTION

PATENT NO. : 5,399,701
DATED : March 21, 1995
INVENTOR(S) : Eugene P. Janulis

Page 1 of 4

It is certified that error appears in the above-indentified patent and that said Letters Patent is hereby corrected as shown below:

Col. 1, line 36     "(HHOBACPC)." should read -- (HOBACPC). --

Col. 1, line 68     "liquid=crystal" should read --liquid crystal--.

Col. 2, line 40     at end of formal insert -- , or --

Col. 4, lines 20-21     "Effort," should read -- Efron --

Col. 4, line 46     "$\pi\Delta and/\lambda=\pi/2$" should read -- $\pi\Delta nd/\lambda=\pi/2$ --

Col. 5, line 50     insert before first formula "D is"

Col. 5, lines 61-62,     "$-OC_qH_{2q}-OC_{q'}H_{2q'+1'}$ $-C_qH_{2q}-O-C_{q'}H_{2'+1'}-C_qH_{2q}-R'$ "

should read

-- $-OC_qH_{2q}-OC_{q'}H_{2q'+1'}$ $-C_qH_{2q}-O-C_{q'}H_{2q'+1'}-C_qH_{2q}-R'$,--.

Col. 6, lines 3-5     first formula "$-O\overset{O}{\underset{\|}{C}}C_{q'}H_{2q+1}$" should read -- $-O\overset{O}{\underset{\|}{C}}C_{q'}H_{2q'+1}$.--

Col. 6, line 9,     "$-C_qF_{2q}-O-C_q, F_{2q}, -X,$" should read

-- $-C_qF_{2q}-O-C_{q'}F_{2q'}-X,$ --

UNITED STATES PATENT AND TRADEMARK OFFICE
CERTIFICATE OF CORRECTION

PATENT NO. : 5,399,701
DATED : March 21, 1995
INVENTOR(S) : Eugene P. Janulis

It is certified that error appears in the above-indentified patent and that said Letters Patent is hereby corrected as shown below:

Col. 7, lines 16-43  Delete the "*" from the middle of each formula and move it to a spot above the "O", for example:

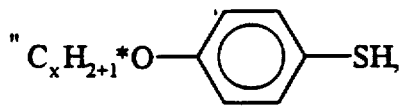

should read

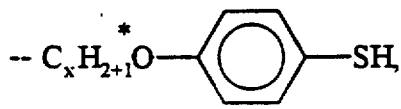

Col. 9, lines 55-56  " $—OC_qH_{2q}—OC_{q'}H_{2q'+1}$, $—C_qH_{2q}—O—_q, H_{2q'+1},$ "

should read

-- $—OC_qH_{2q}—OC_{q'}H_{2q'+1}$, $—C_qH_{2q}—O—C_{q'}H_{2'+1}$, --

Col. 9, lines 65-67, first formula " $—O\overset{\underset{\|}{O}}{C}C_{q'}H_{2q'+1}$ " should read -- $—O\overset{\overset{O}{\|}}{C}C_{q'}H_{2q'+1}$ --

Col. 10, line 18,  " $—C_qF_{2q}—O—C_q, F_{2q}, —X,$" should read

-- $—C_qF_{2q}—O—C_{q'}F_{2q'}—X,$ --

UNITED STATES PATENT AND TRADEMARK OFFICE
CERTIFICATE OF CORRECTION

PATENT NO. : 5,399,701             Page 3 of 4
DATED : March 21, 1995
INVENTOR(S) : Eugene P. Janulis It is certified that error appears in the above-indentified patent and that said Letters Patent is hereby corrected as shown below:

| | |
|---|---|
| Col. 12, line 33 | "for day." should read -- for 1 day. -- |
| Col. 12, line 34 | "HHCl." should read -- HCl. -- |
| Col. 14, line 1 | "monobenzylhyaroquinone" should read -- monobenzylhydroquinone -- |
| Col. 15, line 5 | " 1,1-dihydroperfluorobutyltrifluoromethyl-" should read -- 1,1-dihydroperfluorobutyl trifluoromethyl- -- |
| Col. 15, line 57 | "portions upon" should read -- portions. Upon -- |
| Col. 17, line 5 | "added upon" should read -- added. Upon -- |
| Col. 17, line 21 | "yloxy)-1napthol" should read -- yloxy)-1-napthol -- |
| Col. 18, line 45 | "droperfluorobutyloxy )-3-pyridinecarboxylic" should read -- droperfluorobutyloxy)-3-pyridinecarboxylic -- |
| Col. 18, line 53 | " S-4=(2- " should read -- S-4-(2- -- |
| Col. 19, line 22 | " 4'-(1,1rdihydroperfluorobutoxy)benzoate." should read -- 4'-(1,1-dihydroperfluorobutoxy)benzoate. -- |
| Col. 19, line 68 | " 2'=[6'-(1,1- " should read -- 2'-[6'-(1,1- -- |

UNITED STATES PATENT AND TRADEMARK OFFICE
CERTIFICATE OF CORRECTION

PATENT NO. : 5,399,701
DATED : March 21, 1995
INVENTOR(S) : Eugene P. Janulis

It is certified that error appears in the above-indentified patent and that said Letters Patent is hereby corrected as shown below:

| | |
|---|---|
| Col. 21, line 20 | "um=sulfate," should read --um sulfate.--. |
| Col. 21, line 55 | "B mmol), should read -- 5 mmol), -- |
| Col. 21, line 56 | "i" should read -- 1 -- |
| Col. 22, line 52 | "HHCl," should read -- HCl, -- |
| Col. 25, line 38 | "HHCl," should read -- HCl, -- |
| Col. 42, Table III | in example no 151, " A,C,*,H* " should read -- A, C*, H* -- |
| Col. 43, line 18 | "isotropic..phase" should read -- isotropic phase -- |
| Col. 44, line 13 | "A →C, 50° C." should read -- A →C* 50° C. -- |

Signed and Sealed this

Seventh Day of November, 1995

BRUCE LEHMAN

*Attest:*

*Attesting Officer*  Commissioner of Patents and Trademarks